(12) United States Patent
Timmis et al.

(10) Patent No.: US 7,964,404 B2
(45) Date of Patent: Jun. 21, 2011

(54) METHODS FOR INCREASING GERMINATION VIGOR BY EARLY SINGULATION OF CONIFER SOMATIC EMBRYOS

(75) Inventors: Roger Timmis, Olympia, WA (US); James A Grob, Bonnie Lake, WA (US); Pramod K Gupta, Federal Way, WA (US); Susan D Rayfield, Auburn, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 238 days.

(21) Appl. No.: 12/164,291

(22) Filed: Jun. 30, 2008

(65) Prior Publication Data

US 2009/0007303 A1 Jan. 1, 2009

Related U.S. Application Data

(60) Provisional application No. 60/947,029, filed on Jun. 29, 2007.

(51) Int. Cl.
 *C12N 5/04* (2006.01)
 *C12N 5/02* (2006.01)
 *A01H 7/00* (2006.01)

(52) U.S. Cl. ............... 435/422; 435/430.1; 435/430

(58) Field of Classification Search ............ 435/430
See application file for complete search history.

(56) References Cited

U.S. PATENT DOCUMENTS

| | | | |
|---|---|---|---|
| 5,294,549 A * | 3/1994 | Pullman et al. ............ | 435/422 |
| 2004/0072143 A1 | 4/2004 | Timmis | |
| 2004/0267457 A1 | 12/2004 | Timmis | |
| 2005/0026281 A1 | 2/2005 | Gupta et al. | |
| 2005/0198713 A1 | 9/2005 | Gupta et al. | |
| 2006/0260015 A1 | 11/2006 | Becwar | |
| 2007/0099923 A1 | 5/2007 | Cheng | |
| 2007/0101463 A1 | 5/2007 | Gupta | |

OTHER PUBLICATIONS

Jens Viktor Norgaard Somatic embryo maturation and plant regeneration in *Abies nordmanniana* L.k Plant Science 124 (1997) 211-221.*

Gupta, P.K., et al., "Forestry in the 21st century: The biotechnology of somatic embryogenesis" Bio/Technology 1993 US LNKD-DOI: 10.1038/NBT0493-454, vol. 11, No. 4, 1993, pp. 454-459, XP002588403 ISSN: 0733-222X.

Grob, J.A., et al., "Dimensional Model of Zygotic Douglas-Fir Embryo Development," International Journal of Plant Sciences 160(4):653-662, Jul. 1999.

Nagmani, R., et al., "Anatomical Comparison of Somatic and Zygotic Embryogeny in Conifers," in S.M. Jain et al. (eds.), Somatic Embryogenesis in Woody Plants, Forestry Sciences, vol. 44, 1995, pp. 23-48.

* cited by examiner

*Primary Examiner* — Annette H Para
(74) *Attorney, Agent, or Firm* — Christensen O'Connor Johnson Kindness PLLC

(57) ABSTRACT

In one aspect, a method is provided for increasing germination vigor of conifer somatic embryos produced in vitro. The method comprises (a) singulating a plurality of individual immature conifer somatic embryos from a first culture of embryos after a first incubation period in a first development media; and (b) contacting the plurality of singulated immature conifer somatic embryos with a second development media for a second incubation period.

19 Claims, 11 Drawing Sheets

METHODS FOR INCREASING GERMINATION VIGOR BY EARLY SINGULATION OF CONIFER SOMATIC EMBRYOS

CROSS REFERENCE TO RELATED APPLICATION

The present application claims the benefit of U.S. Provisional Application No. 60/947,029, filed Jun. 29, 2007.

FIELD OF THE INVENTION

The present invention relates to methods for increasing germination frequency and vigor by early singulation of conifer somatic embryos.

BACKGROUND OF THE INVENTION

The demand for coniferous trees, such as pines and firs, to make wood products continues to increase. One proposed solution to the problem of providing an adequate supply of coniferous trees is to identify individual coniferous trees that possess desirable characteristics, such as a rapid rate of growth, and to produce numerous, genetically identical, clones of the superior trees by somatic cloning.

Somatic cloning is the process of creating genetically identical trees from tree somatic tissue. Tree somatic tissue is tree tissue other than the male and female gametes. In one approach to somatic cloning, tree somatic tissue is cultured in an initiation medium which includes hormones, such as auxins and/or cytokinins, that initiate formation of embryogenic cells that are capable of developing into somatic embryos. The embryogenic cells are then further cultured in a maintenance medium that promotes multiplication of the embryogenic cells to form pre-cotyledonary embryos (i.e., embryos that do not possess cotyledons). The multiplied embryogenic cells are then cultured in a development medium that promotes development and maturation of cotyledonary somatic embryos which can, for example, be placed within artificial seeds and sown in the soil where they germinate to yield conifer seedlings. The seedlings can be transplanted to a growth site for subsequent growth and eventual harvesting to yield lumber, or wood-derived products. Alternatively, the cotyledonary somatic embryos can also be germinated in a germination medium, and thereafter transferred to soil for further growth.

A continuing problem with somatic cloning of conifer embryos is stimulating efficient and cost-effective formation of somatic embryos that are capable of germinating to yield plants. Preferably, conifer somatic embryos, formed in vitro, are physically and physiologically similar, or identical, to conifer zygotic embryos formed in vivo in conifer seeds. There is, therefore, a continuing need for methods for producing viable conifer somatic embryos from conifer embryogenic cells.

SUMMARY OF THE INVENTION

In one aspect, a method is provided for increasing germination vigor of conifer somatic embryos produced in vitro. The method comprises (a) singulating a plurality of individual immature conifer somatic embryos from a first culture of embryos after a first incubation period in a first development media; and (b) contacting the plurality of singulated immature conifer somatic embryos with a second development media for a second incubation period.

In another aspect, a method is provided for producing mature conifer somatic embryos. The method comprises (a) culturing conifer somatic cells in, or on, an induction medium to yield embryogenic cells; (b) culturing the embryogenic cells prepared in step (a) in, or on, a maintenance medium to multiply the embryogenic cells and form pre-cotyledonary conifer somatic embryos; (c) culturing the pre-cotyledonary conifer somatic embryos formed in step (b) in, or on, a first development medium for a first incubation period; (d) singulating a plurality of the conifer somatic embryos incubated in step (c); and (e) incubating the plurality of singulated conifer somatic embryos on a second development medium for a second incubation period.

The methods of the present invention are useful for preparing mature conifer somatic embryos with increased germination frequency and vigor that can be further characterized, such as by genetic or biochemical means, and/or can be germinated to produce conifers, if so desired. Thus, for example, the methods of the invention can be used to more efficiently produce clones of individual conifers that possess one or more desirable characteristics, such as a rapid growth rate or improved wood quality.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

Figure 10:
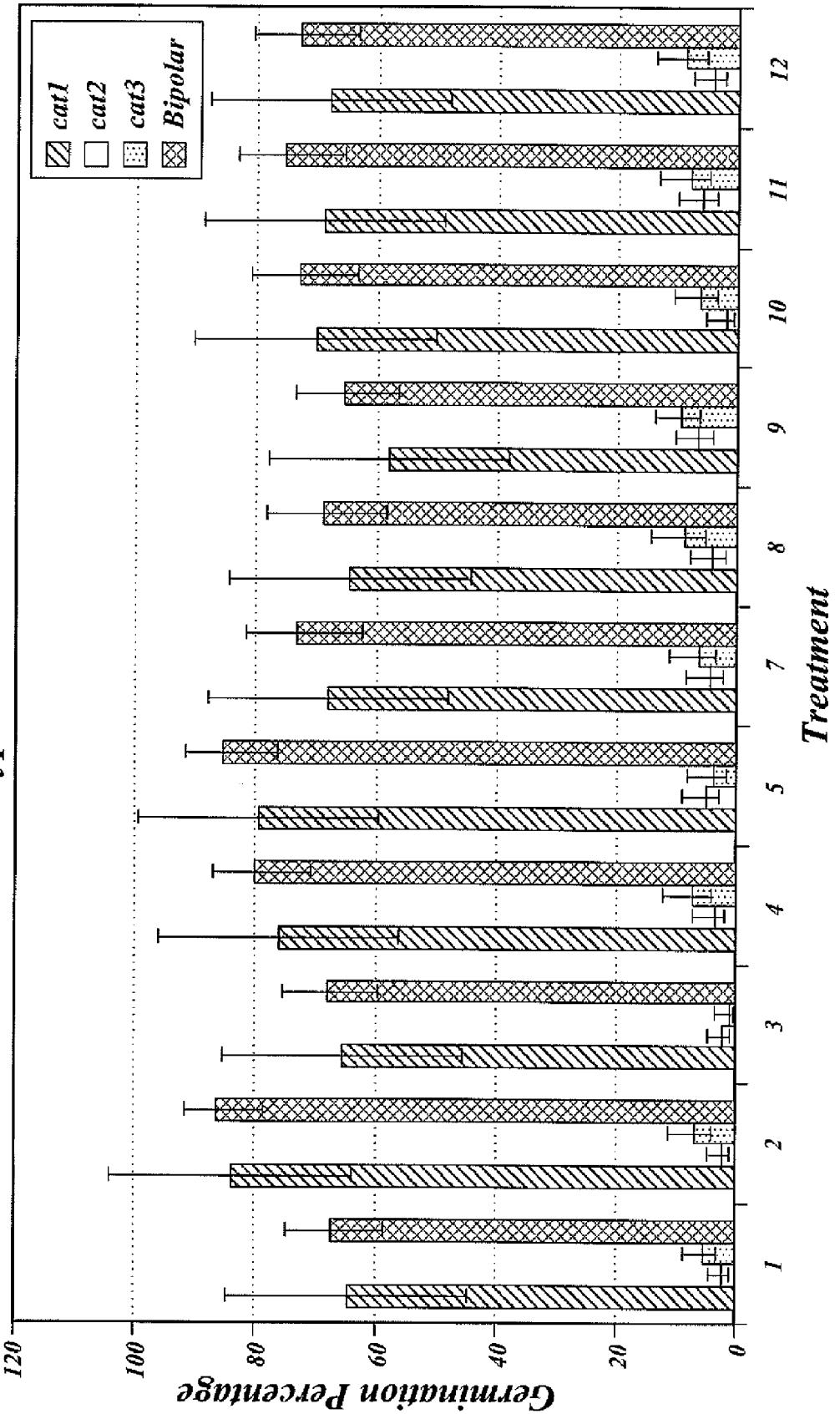
Figure 11:
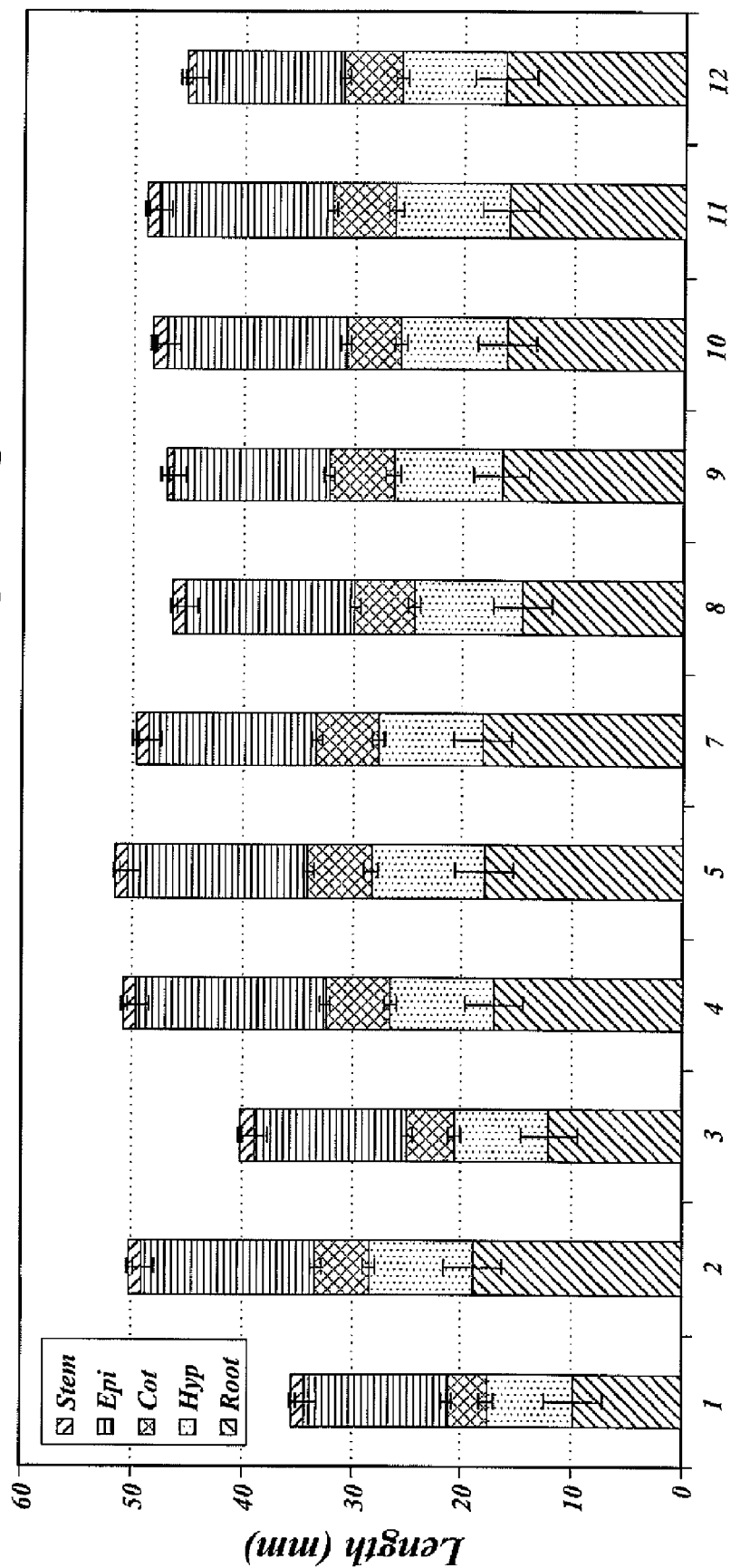

FIG. 10 graphically illustrates the germination percentages for genotype C by treatment described in TABLE 5 with regard to Category 1, 2, and 3 germinants and bipolar germinants, as described in EXAMPLE 3; and FIG. 11 graphically illustrates the data for genotype C for Category 1 germinants by treatment described in TABLE 5 with regard to germinant root length, hypocotyl length, cotyledon length, epicotyl length and epicotyl stem length, as described in EXAMPLE 3.

DETAILED DESCRIPTION OF THE PREFERRED EMBODIMENT

Unless specifically defined herein, all terms used herein have the same meaning as they would to one skilled in the art of the present invention.

As used herein, the term "development stage" refers to the period during somatic cloning during which histogenesis and growth of tissues and organs occurs in an immature embryo to reach a full-sized mature embryo capable of germination into a plant.

As used herein, the term "immature embryo" refers to an embryo that is not yet capable of germination into a plant, and includes embryos in early stage development (i.e., pre-cotyledonary embryos), and mid-stage development (i.e., embryos with cotyledons or hypocotyls that are not yet fully developed).

As used herein, the term "anatomical maturity" refers to an embryo that possesses developed cotyledons and hypocotyl.

As used herein, the term "cotyledonary embryo" refers to an embryo with a well-defined, elongated bipolar structure with latent meristematic centers having one or more clearly visible cotyledonary primordia at one end and a latent radicle at the opposite end.

As used herein, the term "pre-cotyledonary embryo" refers to an embryo that does not yet have cotyledons.

As used herein, the term "normal germinant" denotes the presence of all expected parts of a plant at time of evaluation. The expected parts of a plant may include a radicle, a hypocotyl, one or more cotyledon(s), and an epicotyl. In the case of gymnosperms, a normal germinant is characterized by the radicle having a length greater than 3 mm and no visibly discernable malformations compared to the appearance of embryos germinated from natural seed.

As used herein, the term "radicle" refers to the part of a plant embryo that develops into the primary root of the resulting plant.

As used herein, the term "hypocotyl" refers to the portion of a plant embryo or seedling located below the cotyledons but above the radicle.

As used herein, the term "epicotyl" refers to the portion of the seedling stem that is above the cotyledons.

As used herein, the term "embryonal suspensor mass" or "ESM" refers to a cell mass plated onto the surface of nutrient medium contained either in a semi-solid gel or as a liquid in a porous matrix capable of providing physical support, and left to grow for a period up to three months. During the three month incubation time, somatic embryos grow from microscopic precursor cell groups into visible early-stage embryos and eventually to anatomically mature embryos. The structure of the ESM after several weeks of incubation typically consists of a proliferated mat with a few embryos sitting in direct contact with media, but most embryos forming on the top or side of the still proliferating cell mass.

Unless stated otherwise, all concentration values that are expressed as percentages are weight per volume percentages.

In accordance with the methods of the invention, it has been unexpectedly discovered that singulating immature embryos at mid-development stage (also referred to as early singulation) of somatic embryo production, followed by incubating the singulated embryos on development media for an additional period of time, produces embryos that germinate at an increased frequency and/or vigor, as compared to embryos that are singulated after completing the development stage (mature embryos), as described in more detail in EXAMPLE 2 and EXAMPLE 3 and shown in FIGS. 2-11.

In accordance with the foregoing, in one aspect, a method is provided for increasing germination vigor of conifer somatic embryos produced in vitro. The method comprises: (a) separating a plurality of individual immature conifer somatic embryos from a first culture of embryos after a first incubation period in a first development media; and (b) contacting the plurality of separated immature conifer somatic embryos with a second development media for a second incubation period.

The methods of the invention can be used to produce cotyledonary somatic embryos from any conifer, such as members of the genus *Pinus*, such as Loblolly pine (*Pinus taeda*) and Radiata pine. Again, by way of example, Douglas fir embryos can be produced by the methods of the invention.

A population of mature conifer somatic embryos produced according to the methods of the invention has a greater efficiency of germinating into conifer plants than a population of conifer somatic embryos produced according to an otherwise identical control method that does not include the step of singulating the immature embryos during development.

Figure 1:
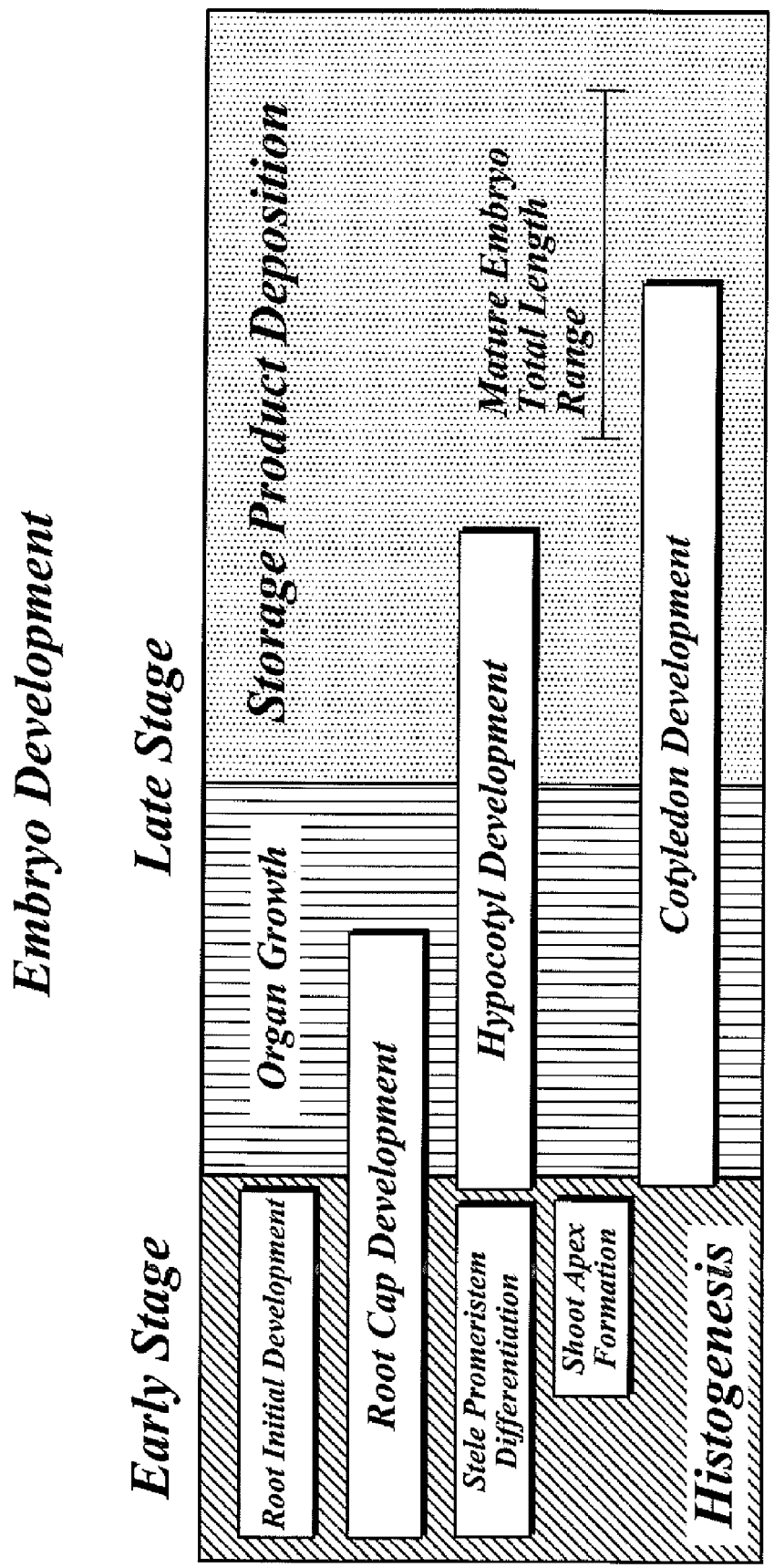
FIG. 1 is a diagrammatic representation of early and late stage development of conifer somatic embryos.

In accordance with the methods of the invention, prior to singulation, a first culture of immature embryos is incubated in a first development media, for a first incubation period. As shown in FIG. 1, the development stage of somatic embryos may be divided into the early stage which involves histogenesis (i.e., the formation of different tissues from undifferentiated cells), mid-stage which involves organ growth and the initiation of hypocotyl development and cotyledon development, and the late stage which involves the completion of organ growth, the completion of hypocotyl and cotyledon development (i.e., anatomical maturity) and storage product deposition. In particular, early stage development of an immature embryo includes root initial development, the beginning of root cap development, stele promeristem differentiation, and shoot apex formation. Mid-stage development includes the initiation of hypocotyl development and cotyledon development, and late stage development includes completion of hypocotyl development and cotyledon development, resulting in an anatomically mature embryo.

In accordance with the methods of the invention, immature conifer somatic embryos, such as, for example, pre-cotyledonary conifer somatic embryos, can be prepared from conifer somatic cells, such as cells obtained from conifer embryos. For example, cells from conifer embryos can be induced by hormones to form embryonal suspensor cell masses (ESMs) that can be treated in accordance with the present invention to yield mature conifer somatic embryos. ESMs can be prepared, for example, from pre-cotyledonary embryos removed from seed. For example, the seed are surface sterilized before removing the pre-cotyledonary embryos, which are then cultured on, or in, an induction medium that permits formation of ESMs which include early state embryos in the process of multiplication by budding and cleavage. ESMs are typically cultured in a maintenance medium to form pre-cotyledonary somatic embryos. Non-limiting examples of ESM culture conditions and suitable induction and maintenance media are further described below.

In one embodiment of the method of the invention, a first culture comprising immature embryos, such as ESM comprising a plurality of pre-cotyledonary somatic embryos, are cultured in, or on, a first development medium that promotes the development of cotyledonary embryos for a first incubation period prior to singulation.

In some embodiments, the first incubation period is sufficient in length for the formation of at least one of the following structures on a portion (e.g., at least one embryo, at least 10% of the embryos, at least 25%, at least 50%, more than 50%, or at least 75%) of the plurality of embryos in the first embryo culture: one or more embryos with cotyledonary primordia; one or more embryos with cotyledons; one or more embryos with 4+ cotyledons; or one or more embryos with distinct cotyledons with hypocotyl and root regions present.

The formation of one or more structures on one or more embryos (e.g., cotyledonary primordial or cotyledons) may be determined by visual inspection or imaging analysis of the cultured embryos. Visual inspection or imaging analysis may be optionally carried out under 5-10× magnification.

The first incubation period may be different depending on the genotype. In some embodiments, the first incubation period is from at least six weeks to at least eight weeks in length, such as from seven to eight weeks. The first incubation on the first development media may be carried out at a temperature from 10° C. to 30° C., such as from 15° C. to 25° C., or such as from 20° C. to 23° C. The first incubation period useful for a particular genotype may be determined using the methods described in EXAMPLE 3.

At the end of the first incubation period, for example, when the presence of one or more cotyledonary primordia is observed on a portion of embryos, or after a time period of at least six weeks, the method comprises singulating a plurality of individual embryos from the first culture of embryos.

Any means of physically separating individual embryos from the first culture of embryos may be used to singulate the embryos in accordance with the methods of the invention. For example, in the context of an embryonal suspensor mass (ESM) culture, physical methods of separation may be used, such as washing away the ESM (e.g., spray singulation via pressure-controlled spray of aqueous liquid), vacuuming away the ESM, vibration, or picking the embryos from the ESM. Other non-limiting examples of useful singulation methods include filtering or sorting embryos based on a physical attribute such as size, shape, for example through a sieve, or based on other physical attributes such as surface roughness, hydrophobicity, density or mass.

In some embodiments, the singulation step further comprises picking individual embryos based on one or more selection criteria. For example, visually evaluated screening criteria may be used by a skilled technician or a computerized imaging system to select embryos based on one or more morphological features including, but not limited to, the embryo's size, shape (e.g., axial symmetry), surface texture, color (e.g., no visible greening), absence of split hypocotyls, and no translucent cotyledons. Embryos can also be selected based on criteria relating to chemistry or external structure adsorption, reflectance, transmittance, or emission spectra through the use of near infrared spectroscopy (NIR), as described in U.S. Patent Application No. 2004/0072143 entitled "Methods for Classification of Somatic Embryos," incorporated herein by reference.

Desirable embryos may be individually picked (via a manual or automated process) out of the first embryo culture (e.g., such as an embryonal suspensor mass), with any suitable instrument, such as tweezers. The embryo picking may be carried out manually or via an automated process, such as described in U.S. Patent Application No. 2004/0267457, entitled "Automated System and Method for Harvesting and Multi-Stage Screening of Plant Embryos," incorporated herein by reference.

In some embodiments of the method, the picked embryos are laid out directly onto the surface of a second development medium, or onto a porous substrate in contact with a second development medium, which may be in solid or liquid form.

A porous substrate that is useful in the practice of various embodiments of the methods of the invention typically has a pore diameter in the range of from about 5 microns to about 1200 microns, such as from about 50 to 500 microns, such as from about 70 to about 150 microns, such as about 100 microns. The porous material is typically planar and may be any desired shape or dimension chosen for ease of manipulation and for placement in contact with the second development media. Exemplary porous materials include materials that are sterilizable and sufficiently strong to resist tearing when the materials are lifted in order to transfer singulated embryos to subsequent stages of the somatic embryo production process, such as stratification. Examples of useful porous materials include, but are not limited to, membranes, nylon fiber, woven mesh (e.g., nylon, stainless steel or plastic), and polymeric fibers.

In some embodiments, the singulated embryos are transferred to a second development media, or a porous substrate in contact with a second development media, in such a manner that the singulated embryos are not in physical contact with one another. As described in EXAMPLE 2 and EXAMPLE 3, it has been shown that embryos developing in association with other embryos in an embryonal suspensor mass experience a microenvironment that is inhibitory to full embryo development.

In some embodiments, the singulated embryos are contacted with a second development media that is previously cell-contacted (used). In some embodiments, the singulated embryos are contacted with a second development media that is a previously cell-contacted first development media, such as the cell-contacted development media used during the first incubation period. For example, in the context of an embryonal suspensor mass culture incubated on a first development medium, after the first incubation period, a plurality of individual immature embryos may be singulated via a spray singulation method, resulting in the transfer of individual singulated embryos onto a surface of the previously cell-contacted first development medium.

According to the methods of the invention, after singulation, the singulated immature embryos are contacted with a second development medium for a second incubation period. In some embodiments, the second incubation period is sufficient in length for at least a portion (e.g., at least one embryo, at least 10% of the embryos, at least 25%, at least 50%, more than 50%, or at least 75%) of the plurality of singulated embryos to reach anatomical maturity (i.e., possessing developed cotyledons and hypocotyl).

The second incubation period may be different depending on the genotype. In some embodiments, the second incubation period is from at least three weeks in length, such as three to five weeks. In some embodiments, the embryos are incubated for a total length of time (including the first incubation period and the second incubation period) of at least 12 weeks on development media. The second incubation on the second development media may be carried out at a temperature from 10° C. to 30° C., such as from 15° C. to 25° C., or such as from 20° C. to 23° C. The second incubation period useful for a particular genotype may be determined using the methods described in EXAMPLE 3.

The first and second development media typically contain nutrients that sustain the somatic embryos. Suitable development media typically do not include growth-promoting hormones, such as auxins and cytokinins. In some embodiments, the first and second development media have the same formulation. In some embodiments, the first and second development media have different formulations.

The osmolality of the first and/or second development medium can be adjusted to a value that falls within a desired range, such as from about 250 mM/Kg to about 450 mM/Kg. Typically, an osmolality of 350 mM or higher is advantageous in the methods of the invention. An example of a suitable development medium BM3 is set forth in EXAMPLE 1 herein. Another example of a suitable development medium devB is set forth in EXAMPLE 3 herein. In some embodiments of the method, the second development medium has a higher osmolality (e.g., from 350 mM/Kg to 450 mM/Kg) than the first development medium (e.g., from 300 mM/Kg to 400 mM/Kg). In some embodiments, the osmolality of the second development media is chosen to match the osmolality of the first development media at the end of the first incubation period.

In some embodiments, the first and/or second development medium comprises PEG at a concentration from 1% to 15%. In some embodiments, the first development medium comprises PEG at a concentration of 7% to 10% (e.g., 7%, 8%, 9%, 10%). In some embodiments, the second development medium comprises PEG at a concentration of 8% to 15% (e.g., 8%, 9%, 10%, 11%, 12%, 13%, 14%, 15%). In some embodiments, the second development medium comprises PEG at a higher concentration than the first development medium.

Maltose may be included in the first and/or second development medium as the principal or sole source of sugar for the somatic embryos. Useful maltose concentrations are within the range of from about 1% to about 2.5%.

The first and/or second development medium may contain gellan gum. Gellan gum is a gelling agent marketed, for example, under the names GELRITE and PHYTAGEL. If gellan gum is included in the development medium, it is typically present at a concentration less than about 0.5%, typically at a concentration from about 0% to about 0.4%. The first and second development media are typically a solid medium, although one or both can be a liquid medium.

The first and/or second development medium may contain an absorbent composition, such as activated charcoal, as described herein, for the induction medium. An exemplary maturation medium is set forth as devB in EXAMPLE 3.

In some embodiments, the first and/or second development medium further comprises sucrose and/or abscisic acid. The concentration of abscisic acid in the development medium may be between 0.5 mg/L and 500 mg/L. In some embodiments of the methods of the invention, the concentration of abscisic acid in the development medium is between 1 mg/L and 100 mg/L. In some embodiments, the concentration of abscisic acid in the development medium is between 5 mg/L and 20 mg/L.

In some embodiments of the invention, the first and/or second development medium contains sucrose as the principal or sole source of metabolizable sugar. Useful sucrose concentrations are within the range of about 1% to about 6%.

In some embodiments, after incubation in the second development medium, the singulated embryos are then cultured in, or on, a stratification medium for a period of about one week to about six weeks, at a temperature of from about 1° C. to about 10° C. Typically, the stratification medium is similar or identical to the development medium, but does not contain abscisic acid and has a lower concentration of gellan gum, typically less than about 0.5%. The stratification medium may contain sucrose as the principal or sole source of metabolizable sugar. An exemplary stratification medium is set forth as $BM_5$ in EXAMPLE 1.

In some embodiments, the present invention provides methods for producing mature conifer somatic embryos, comprising the steps of: (a) culturing conifer somatic cells in, or on, an induction medium to yield embryogenic cells; (b) culturing the embryogenic cells prepared in step (a) in, or on, a maintenance medium to multiply the embryogenic cells and form pre-cotyledonary conifer somatic embryos; (c) culturing the pre-cotyledonary conifer somatic embryos formed in step (b) in, or on, a first development medium for a first incubation period; (d) singulating a plurality of the conifer somatic embryos incubated in step (c); and (e) incubating the plurality of singulated conifer somatic embryos on a second development medium for a second incubation period.

Thus, in some embodiments, conifer somatic cells are cultured in, or on, an induction medium to yield embryogenic cells. Embryogenic cells are cells that are capable of producing one or more cotyledonary conifer somatic embryos and include, for example, conifer embryonal suspensor masses. The induction medium typically includes inorganic salts and organic nutrient materials. The osmolality of the induction medium is typically about 160 mg/kg or even lower, but it may be as high as 170 mM/kg. The induction medium typically includes growth hormones. Examples of hormones that can be included in the induction medium are auxins (e.g., 2,4-dichlorophenoxyacetic acid (2,4-D)) and cytokinins (e.g., 6-benzylaminopurine (BAP)). Auxins can be utilized, for example, at a concentration of from 1 mg/L to 200 mg/L. Cytokinins can be utilized, for example, at a concentration of from 0.1 mg/L to 10 mg/L.

The induction medium may contain an absorbent composition, especially when very high levels of growth hormones are used. The absorbent composition can be any composition that is not toxic to the embryogenic cells at the concentrations utilized in the practice of the present methods, and that is capable of absorbing growth-promoting hormones, and toxic compounds produced by the plant cells during embryo development, that are present in the medium. Non-limiting examples of useful absorbent compositions include activated charcoal, soluble poly(vinyl pyrrolidone), insoluble poly(vinyl pyrrolidone), activated alumina, and silica gel. The absorbent composition may be present in an amount, for example, of from about 0.1 g/L to about 5 g/L. An example of an induction medium useful in the practice of the present invention is medium $BM_1$ set forth in EXAMPLE 1 herein. The induction medium is typically solid, and may be solidified by inclusion of a gelling agent.

Conifer somatic cells are typically cultured in, or on, an induction medium for a period of from three weeks to ten weeks, such as from six weeks to eight weeks, at a temperature of from 10° C. to 30° C., such as from 15° C. to 25° C., or such as from 20° C. to 23° C.

The maintenance medium may be a solid medium, or it may be a liquid medium which can be agitated to promote growth and multiplication of the embryogenic tissue. The osmolality of the maintenance medium is typically higher than the osmolality of the induction medium, typically in the range of 180-400 mM/kg. The maintenance medium may contain nutrients that sustain the embryogenic tissue, and may include hormones, such as one or more auxins and/or cytokinins, that promote cell division and growth of the embryogenic tissue. Typically, the concentrations of hormones in the maintenance medium is lower than their concentration in the induction medium.

It is generally desirable, though not essential, to include maltose as the sole, or principal, metabolizable sugar source in the maintenance medium. Examples of useful maltose concentrations are within the range of from about 1% to about 2.5%. An example of a suitable maintenance medium is medium $BM_2$ set forth in EXAMPLE 1 herein. Conifer embryogenic cells are typically transferred to fresh maintenance medium once per week.

As described above, pre-cotyledonary conifer somatic cells formed from conifer embryogenic cells are cultured in, or on, a first development medium for a first incubation period, singulated, and then cultured on a second development medium for a second incubation period. Useful development media and incubation time periods are described supra.

After being cultured in the second development media, the cotyledonary somatic embryos can optionally be transferred to a stratification medium, for a further period of culture.

The conifer cotyledonary somatic embryos produced using the methods of the invention can optionally be germinated to form conifer plants which can be grown into coniferous trees, if desired. The cotyledonary embryos may also be disposed within artificial seeds for subsequent germination. The conifer cotyledonary somatic embryos can be germinated, for example, on a solid germination medium, such as the germination medium described in EXAMPLE 1 herein. The germinated plants can then be transferred to soil for further growth. For example, the germinated plants can be planted in soil in a greenhouse and allowed to grow before being transplanted to an outdoor site. Typically, the conifer cotyledonary somatic embryos are illuminated to stimulate germination.

The methods of the invention produce a population of mature conifer somatic embryos with a capacity to germinate at a higher frequency (i.e., produce a higher yield of germinants) than a population of conifer somatic embryos produced according to an otherwise identical method that does not include the step of singulating immature embryos during development. Some embodiments of the methods of the invention yield mature conifer somatic embryos that have a germination efficiency that is at least 100% higher (e.g., between 100% and 200% higher) than the germination efficiency of mature conifer somatic embryos produced according to an otherwise identical method that does not include the step of singulating immature cotyledonary conifer somatic embryos during development, as further described in EXAMPLES 2-3 and shown in FIGS. 2-11, supra.

The following examples merely illustrate the best mode now contemplated for practicing the invention, but should not be construed to limit the invention.

Example 1

This Example describes a method for producing somatic pine embryos from Loblolly Pine using post-development singulation.

Methods:

Female gametophytes containing zygotic embryos are removed from seeds four to five weeks after fertilization. The seed coats are removed but the embryos are not further dissected out of the surrounding gametophyte other than to excise the nucellar end. The cones are stored at 4° C. until used. Immediately before removal of the immature embryos the seeds are sterilized utilizing an initial washing and detergent treatment followed by a ten minute sterilization in 15% $H_2O_2$. The explants are thoroughly washed with sterile distilled water after each treatment.

Tables 1 and 2 set forth exemplary compositions of media useful for producing pine somatic embryos.

TABLE 1

*Pinus Taeda* Basal Medium (BM)

| Constituent | Concentration (mg/L) |
| --- | --- |
| $NH_4NO_3$ | 150.0 |
| $KNO_3$ | 909.9 |
| $KH_2PO_4$ | 136.1 |
| $Ca(NO_3)_2 \cdot 4H_2O$ | 236.2 |
| $CaCl_2 \cdot 4H_2O$ | 50.0 |
| $MgSO_4 \cdot 7H_2O$ | 246.5 |
| $Mg(NO_3)_2 \cdot 6H_2O$ | 256.5 |
| $MgCl_2 \cdot 6H_2O$ | 50.0 |
| KI | 4.15 |
| $H_3BO_3$ | 15.5 |
| $MnSO_4 \cdot H_2O$ | 10.5 |
| $ZnSO_4 \cdot 7H_2O$ | 14.4 |
| $NaMoO_4 \cdot 2H_2O$ | 0.125 |
| $CuSO_4 \cdot 5H_2O$ | 0.125 |
| $CoCl_2 \cdot 6H_2O$ | 0.125 |
| $FeSO_4 \cdot 7H_2O$ | 27.86 |
| $Na_2EDTA$ | 37.36 |
| Maltose | 30,000 |
| myo-Inositol | 200 |
| Casamino acids | 500 |
| L-Glutamine | 1000 |
| Thiamine-HCl | 1.00 |
| Pyridoxine-HCl | 0.50 |
| Nicotinic acid | 0.50 |
| Glycine | 2.00 |
| Gelrite+ | 1600 |
| pH adjusted to 5.7 | |

+Used if a solid medium is desired.

TABLE 2

Composition of Media for Different Stage Treatments

| | |
| --- | --- |
| $BM_1$-Induction Medium | BM + 2,4-D (15 μM) + Kinetin (2 μM) + BAP (2 μM). |
| $BM_2$-Maintenance Medium | BM + 2,4-D (5 μM) + Kinetin (0.5 μM) + BAP (0.5 μM). GELRITE (1600 mg/L) is added when a solid medium is desired. |
| Dilution Medium | BM + 10 mg/mL abscisic acid + 100-1000 mg/mL additional myo-inositol, + 2.5% Maltose. The following amino acid mixture is added: L-proline (100 mg/L), L-asparagine (100 mg/L), L-arginine (50 mg/L), L-alanine (20 mg/L), and L-serine (20 mg/L). Preferably no maintenance hormones are present. |
| $BM_3$-Development Medium A | BM + 25 mg/L abscisic acid + 12% PEG-8000 + 800 mg/L additional myo-inositol + 0.1% activated charcoal + 1% glucose, + 2.5% Maltose. The following amino acid mixture is added: L-proline (100 mg/L), L-asparagine (100 mg/L), L-arginine (50 mg/L), L-alanine (20 mg/L), and L-serine (20 mg/L). GELRITE (2500 mg/L) is added when a solid medium is desired. |
| $BM_5$-Stratification Medium | $BM_3$ modified by omitting abscisic acid, and PEG-8000. GELRITE (2500 mg/L) is added when a solid medium is desired. |
| $BM_6$-Germination Medium | BM modified by replacing maltose with 2% sucrose. Myo-inositol is reduced to 100.0 mg/L, glutamine and casamino acids are |

TABLE 2-continued

Composition of Media for Different Stage Treatments reduced to 0.0 mg/L. $FeSO_4 \cdot 7H_2O$ is reduced to 13.9 mg/L and $Na_2EDTA$ reduced to 18.6 mg/L. Agar at 0.8% and activated charcoal at 0.25% are added.

Induction: Sterile gametophytes with intact embryos are placed on a solid $BM_1$ culture medium and held in an environment at 22°-25° C. with a 24 hour dark photoperiod for a time of three to five weeks. The length of time depends on the particular genotype being cultured. At the end of this time, a white mucilaginous mass forms in association with the original explants. Microscopic examination typically reveals numerous early stage embryos associated with the mass. These are generally characterized as having a long thin-walled suspensor associated with a small head with dense cytoplasm and large nuclei.

Osmolality of the induction medium may in some instances be as high as 150 mM/kg, and is typically about 120 mM/kg or even lower (such as 110 mM/kg).

Maintenance and Multiplication of Pre-cotyledonary Embryos: Early stage embryos removed from the masses generated in the induction stage are first placed on a $BM_2$ gelled maintenance and multiplication medium. This differs from the induction medium in that the growth hormones (both auxins and cytokinins) are reduced by at least a full order of magnitude. Osmolality of this medium is at 130 mM/kg or higher (typically within the range of about 120-150 nM/kg for *Pinus taeda*). The temperature and photoperiod are again 22°-25° C. with 24 hours in the dark. Embryos are cultured 12-14 days on the $BM_2$ solid medium before transferring to a liquid medium for further subculturing. This liquid medium has the same composition as $BM_2$, but lacks the gellant. The embryos at the end of the solid maintenance stage are typically similar in appearance to those from the induction stage. After five to six weekly subcultures on the liquid maintenance medium, advanced early stage embryos have formed. These are characterized by smooth embryonal heads, estimated to typically have over 100 individual cells, with multiple suspensors.

Embryo Development

Early stage immature embryos are transferred to a solid development medium. The development medium either lacks growth hormones entirely, or has them present only at very low levels. Abscisic acid is typically included to facilitate further development. The further inclusion of an absorbent composition in this medium is advantageous. The absorbent composition may be chosen from a number of chemical materials having high surface area and/or controlled pore size, such as activated charcoal, soluble and insoluble forms of poly(vinyl pyrrolidone), activated alumina, and silica gel. The absorbent composition is normally present at a concentration of about 0.1-5 g/L, more generally about 0.25-2.5 g/L. Gellan gum may be included at a concentration of about 0.25%.

The osmotic potential of this development medium may be raised substantially over that of the maintenance medium. It has been found advantageous to have an osmolality as high as 350 mM/kg or even higher. Development is preferably carried out in complete darkness at a temperature of 22°-25° C. until cotyledonary embryos have developed (e.g., reached anatomical maturity).

Stratification: After 7 to 12 weeks on development medium, cotyledonary embryos are singulated and transferred to stratification medium $BM_5$. This medium is similar to development medium but lacks abscisic acid, PEG-8000, and gellan gum. Embryos are cultivated on stratification medium at between about 1° C. and about 10° C. in the dark for between three to six weeks.

Drying: The mature embryos still on their filter paper support are lifted from the pad and placed in a closed container over $H_2O$ at a relative humidity of 97%, for a period of about three weeks.

Germination: The dried mature embryos are rehydrated by placing them, while still on the filter paper support, for about 24 hours on a pad saturated with liquid germination medium. The embryos are then placed individually on solid $BM_6$ medium for germination. This is a basal medium lacking growth hormones which is modified by reducing sucrose, myo-inositol and organic nitrogen. The embryos are incubated on $BM_6$ medium for about ten weeks under environmental conditions of 23°-25° C., and a 16-hour light—8-hour dark photoperiod, until the resulting plantlets have a well developed radicle and hypocotyl and green cotyledonary structure and epicotyl.

Because of the reduced carbohydrate concentration, the osmotic potential of the germination medium may be further reduced below that of the development medium. It is normally below about 150 mM/kg (such as about 100 mM/kg).

Results:

Using the methods described in this example, the typical germination frequencies obtained for three representative genotypes of Loblolly Pine are as follows:

Genotype A: 22% germination frequency.
Genotype B: 12% germination frequency.
Genotype C: 62% germination frequency.

Example 2

This Example describes a series of experiments designed to test the effects of early singulation of immature embryos (during the development stage) on germination frequency.

Methods:

Six different experiments were run to test the effects of early singulation as follows:

Experiment 2.1

Methods: A Loblolly Pine genotype A embryonal suspensor mass culture was incubated on solid development media for 12 weeks and the embryos were assessed. At 12 weeks, one set of small embryos (108 embryos) were left on the same development media plate for an additional two weeks and a second set of small embryos (108 embryos) were moved to ESM-free fresh development media (of the same composition) and grown for an additional two weeks. At the end of the additional two week incubation period (total of 14 weeks on development media), the embryos from the first and second set were assessed for embryo size and germination percentage.

Results: The results of this experiment are summarized in TABLE 3. It was unexpectedly determined that the first set of small embryos (108) that were left undisturbed on the development plate for an additional two weeks did not grow in size from the 12th week to the 14th week on development media and their germination percentage was zero. In contrast, it was unexpectedly discovered that the second set of small embryos (108) that were singulated (hand picked) at 12 weeks, transferred to ESM-free fresh development media (of the original composition), and incubated for an additional two weeks, continued to grow in size and germinated at a rate matching the earlier-harvested embryos (large or small embryos harvested at 12 weeks). Therefore, it appeared that leaving the first set of small embryos undisturbed and mired in the ESM for two additional weeks inhibited embryo vigor and germination potential.

Experiment 2.2 This experiment was carried out as a control in an imaging experiment to determine whether the removal of immature Loblolly Pine embryos of genotype A from development media during development and replacement back onto the same development media (previously cell-contacted) would change the course of development. In this experiment, immature embryos growing on solid development media were singulated (hand picked) at weeks 5, 6, 7, 8, 9, 10 and week 12 of incubation on development media and returned to the same (previously cell-contacted) ESM-free development media. Seven plates of embryos were tested per treatment. After 12 total weeks of incubation on development media the embryos were stratified for two weeks. The embryos were then assessed for germination percentage.

Results: The results of this experiment are summarized in TABLE 3. As shown in TABLE 3, this experiment confirmed the unexpected observation in Experiment 2.1 (described above) that singulation of immature embryos during development stage has a major beneficial effect on germination, with an optimum germination percentage (86%) resulting from embryos that were singulated (picked) from development media at eight weeks and replaced onto the same ESM-free development media. Embryos singulated at 10 or 12 weeks of incubation on development media had a germination percentage of only 48%. As described above in EXAMPLE 1, prior to the methods of the present invention, singulation after 12 weeks on development media at the time of stratification of the embryos was the standard practice. Therefore, the methods of the invention lead to a germination percentage that is nearly twice the germination percentage that was routinely obtained using standard methods.

Experiment 2.3 This experiment was carried out with three different genotypes A, B, and D of Loblolly pine embryos to see if transfer to various new media at eight weeks after incubation on development media would have beneficial effects. Three flasks each of embryos of genotype A, B, and D were plated onto ten plates per treatment per flask. Embryos were either picked at eight weeks and transferred onto fresh development media, or were transferred en masse (on a nylon support) to fresh development media at 12 weeks. For both conditions, the osmolality of the fresh development media was adjusted to match the osmolality of the medium from which the embryos were transferred.

Results: The results of this experiment are summarized in TABLE 3. As shown in TABLE 3, the results for Genotypes A and B were highly significant in favoring an 8 week transfer to fresh development medium in which the osmolality had been adjusted to match where it left off in the old medium, as compared to en masse transfer at 12 weeks. Genotype D produced too few "normal" embryos for a definitive test, but when Category 2 germinants were included in the analysis, it appeared that early singulation showed a reverse germination trend (p=0.075) with the eight week transfer being inferior to standard 12 week harvest. However, if the lower embryo yield/ml were also taken into account, then this decline was significant as measured by germinant yield/ml. It was noted that genotype B also showed a significant drop in embryo yield/ml following eight week transfer, but its germinant yield/ml was nevertheless still much improved. Embryo yield per ml in genotype A was unaffected.

In another experiment, it was also determined that transfers done en masse (no singulation) using the same media described above did not affect germination percentage (data not shown).

Experiment 2.4 Experiment 2.2, described above, was repeated using more genotypes of Loblolly Pine (gentypes A, C, and D) and solid or liquid development media. Genotype A was tested with 9 plates per treatment. Genotype C was tested with 26 plates per treatment. Genotype D was tested with 9 plates per treatment.

Results: The results of this experiment are summarized in TABLE 3. For genotype A it was determined that transfer at eight weeks was optimal, with germination of the control embryos (at 12 week harvest) was only about half of that of the embryos with an 8 week transfer. Low germination of genotype B and D was observed after transfer at eight weeks.

Experiment 2.5 This experiment was carried out to compare 8 week to 12 week singulation for Loblolly Pine genotypes A and C, using spray separation for singulation (rather than hand picking), followed by incubation on various media conditions, including replacement onto used media (previously cell-contacted), or fresh media with fresh osmoticant.

Results: The results of this experiment are shown in TABLE 3. The results were not statistically significant and therefore inconclusive, due to the low germination percentages. It is likely the low germination resulted from the spray separation method which involved sudden osmotic changes and other differences from hand transfer. However, it was observed that embryos that had been transferred to fresh media had 60% longer germinant roots (p=0.003) as compared to embryos that were put onto used media. The spray separation method can be modified with the use of isotonic solution instead of water, to avoid problems associated with exposing embryos to sudden osmotic changes.

Experiment 2.6 This experiment was carried out to compare the effect on germination frequency of singulation of embryos (hand picked) at seven weeks and nine weeks and transfer to fresh solid development medium. In this experiment, the post-singulation development medium was not osmotically adjusted to match the pre-singulation development medium. Embryo transfers were done sequentially from the same plates, allowing for precise split-plate comparisons to be made. A 12 week control consisted of plates from which no embryos had been removed. Additional controls were included for embryos transferred from development media at seven or nine weeks directly to stratification media, followed by conditioning over water and germination (as described in EXAMPLE 1).

Results: The results of this experiment are shown in TABLE 3. It was observed that germination percentages after singulation at seven weeks was 72% as compared to singulation at 9 weeks (43% germination), or as compared to the 12 week control with no singulation (12% germination). The differences observed were large and statistically significant. In addition, the seven week singulated embryos had an embryo dry weight at the end of development that was 3× the dry weight of control germinants (without falling below the minimum water content requirements), with 54% longer roots than control germinants.

Figure 2:
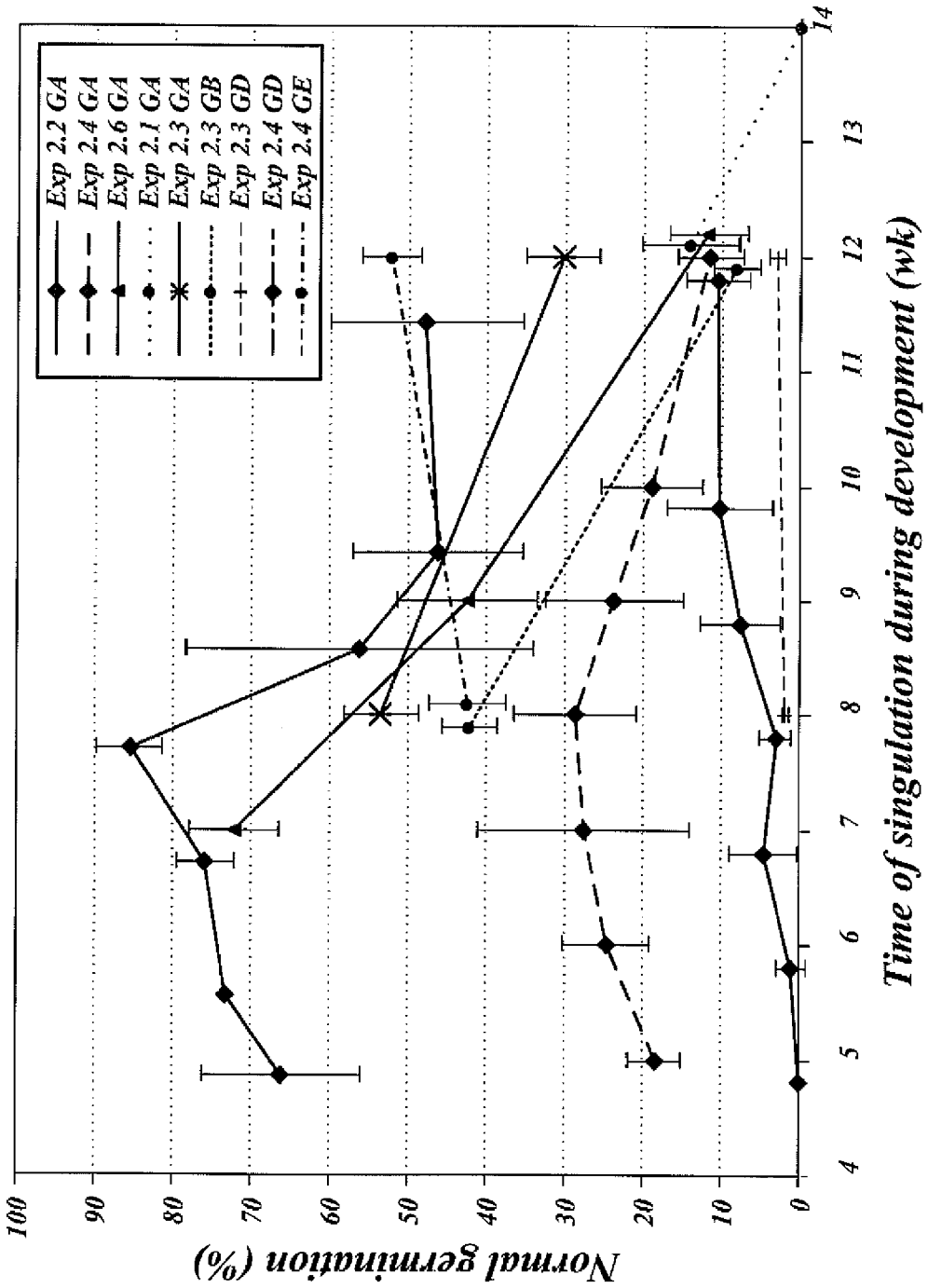
FIG. 2 graphically illustrates the germination results of a series of five experiments in which embryos were transferred by hand (singulated) during development onto fresh or modified media for continued development, as described in EXAMPLE 2.

Overall Summary of Experimental Results: All five experiments using manual singulation (hand picked) of embryos showed a significant effect on one or more measures of embryo quality (e.g., a significant improvement in higher germination percentages, higher germinant per ml yields, greater root growth of germinants and greater embryo dry weight), when embryos were singulated during the development stage transferred to a development medium (either previously cell-contacted medium or fresh medium) for continued development. The results of these experiments are summarized in TABLE 3 and FIG. 2. FIG. 2 graphically illustrates the germination results of the five experiments (2.1, 2.2, 2.3, 2.4 and 2.6) in which embryos were transferred by hand during development, with each genotype ("G") indicated as (genoytpe A, B, D or E) in the figure legend.

As shown in FIG. 2, the optimal week for singulation appears to be between week seven to week ten, with some genotype specific variability observed.

In particular, it was noted that genotype A showed a large improvement in all five experiments. Genotype B showed a large improvement in the experiment in which it was tested. Genotype D showed a decline in the two experiments where it was tested, but the controls produced very low germination percentages. Genotype E showed a modest decline in the one experiment in which it was tested. Genotype C was only tested in an experiment that had inconclusive results due to the confounding effects introduced by spray singulation.

The data from this series of experiments suggests that embryos developing in association with, or on top of ESM experience a microenvironment that is inhibitory to full embryo development, and that singulation during development increases germination vigor of the singulated embryos. While not wishing to be bound by theory, it is also possible that the embryo suspensor mat itself may excrete additional compounds that are inhibitory to embryo development. It is also likely that embryos in the ESM are nourished indirectly, and are in competition with other tissues, such that the nutrient supply rate and chemical composition of media components are reduced in comparison to embryos that are directly contacted with media.

TABLE 3

Summary of results from Experiments 2.1 to 2.6

| | Genotype (Loblolly | Development media | | Germination spec | \multicolumn{7}{c|}{Germination (%) results after singulation at:} | | |
|---|---|---|---|---|---|---|---|---|---|---|---|---|---|
| Exp | Pine) | pre-sing | post-sing | tion spec | 5 wk | 6 wk | 7 wk | 8 wk | 9 wk | 10 wk | 12 wk | 14 wk | Stat Sign p = | type of test |
| 2.1 | A | solid dev (13% PEG) (0.25% gelrite) | same (used) | 12-week incubation (transplant ready) | — | — | — | — | — | — | 14 | — | 0.023 | t test of pre-defined contrast |
| | | | | 12-week incubation (total bipolar = category 1 + category 2) | — | — | — | — | — | — | 36 | 5 | 0.041 | |
| 2.2 | A | solid dev (10% PEG) (0.25% gelrite) | solid dev (used) | 12-week incubation (transplant ready) | 66 | 73 | 76 | 86 | 56 | 46 | 48 | — | 0.011 | F-test of polynomial regression |
| 2.3 | A | liquid dev (12% PEG) | fresh liquid medium (same osmol) | 6 week incubation (normal germinants) | — | — | — | 53 | — | — | 30 | — | <0.0001 | F-tests from ANOVA |
| | B | | | | — | — | — | 42 | — | — | 8 | — | <0.0001 | |
| | D | | | 6-week incubation (total bipolar = category 1 + category 2) | — | — | — | 8 | — | — | 15 | — | 0.075 | |
| 2.4 | A | solid dev (10% PEG) (0.25% gelrite) | solid dev (used) | 6 wk incubation (normal germinants) | 18 | 25 | 28 | 29 | 24 | 19 | 12 | — | <0.01 | F test of polynomial regression |
| | C | solid dev (10% PEG) (0.25% gelrite) | solid dev (used) | 6 wk incubation (normal germinants) | — | — | — | 43 | — | — | 52 | — | <0.01 | F test of linear regression on pooled batches |
| | E | liquid (12% PEG) | liquid (used) | 6 wk incubation (normal germinants) | 0 | 1 | 4 | 3 | 8 | 10 | 10 | — | 0.003 | paired t test of pooled batches |
| 2.5 | A | solid dev (10% PEG) (0.25% gelrite) | same medium (used) | 6-wk incubation (normal germinants) | — | — | — | 11 | — | — | 14 | — | n.s. | |
| | | | fresh medium (fresh osmo) | | — | — | — | 12 | — | — | 14 | — | n.s. | data inspection of either normals or total bipol |
| | C | | same medium (used) | 6-wk incubation (total bipolar = category 1 + category 2) | — | — | — | 6 | — | — | 2 | — | n.s. | |
| | | | fresh medium (fresh osmo) | | — | — | — | 11 | — | — | 2 | — | n.s. | ANOVA |
| 2.6 | A | solid dev (10% PEG) (0.25% gelrite) | solid fresh medium (fresh osmol) | 6 week incubation (normal germinants) | — | — | 72 | — | 43 | — | 12 | — | <0.0001 | t-tests, paired and unpaired |

Example 3

This Example demonstrates the dramatic improvement in germination frequencies observed when immature embryos were singulated during embryo development and the effect of incubating post-singulated embryos on development media with various Gelrite/PEG concentrations.

Rationale: An experiment was set up to examine the effect on germination percentages of embryos that were either moved en masse after development or individually picked (singulated) to fresh media during mid-development.

Methods:

Induction and Maintenance of Pre-Cotyledonary Embryos:

Somatic embryos from three different genotypes (A, B, and C of Loblolly Pine) were induced as described in Example 1 and were maintained in maintenance media M2: (BM medium TABLE 2+1.1 mg/L 2,4D; 0.1 mg/mL 6-BAP, 0.1 mg/mL kinetin, and 1 mg/mL ABA).

Pre-Singulation Embryo Development:

Pre-cotyledonary embryos from each genotype (A, B, and C) were plated onto ½ size (3.91 liter) food preparation boxes (Cambro Company) containing 600 ml semi-solid development media B (dev B), described below in TABLE 4. To each box, 24 individual 100 micron nylon mesh squares (1.5×1.5 inches) were added to permit undisturbed removal of the entire culture at 7-8 weeks of development.

Conifer somatic embryo cells of each genotype (A, B, and C) that were grown in maintenance medium M2 in 1 liter flasks were allowed to settle. The settled cell volume (SCV) was measured by drawing a line on the flask, and supernatant above the settled cells was withdrawn via a fritted glass wand under aspiration. The settled cells were then resuspended in a wash solution, allowed to settle again, and one drop of 0.5 ml SCV was added to each mesh square. Four ½ cambro boxes were plated per genotype, with 12 mls of SCV plated on each.

TABLE 4

| Loblolly Solid Development Media (Dev B) | |
| --- | --- |
| Constituent | Concentration (mg/L) |
| $NH_4NO_3$ | 150.0 |
| $KNO_3$ | 909.9 |
| $KH_2PO_4$ | 136.1 |
| $Ca(NO_3)_2 \cdot 4H_2O$ | 236.2 |
| $CaCl_2 \cdot 4H_2O$ | 50.0 |
| $MgSO_4 \cdot 7H_2O$ | 246.5 |
| $Mg(NO_3)_2 \cdot 6H_2O$ | 256.5 |
| $MgCl_2 \cdot 6H_2O$ | 50.0 |
| KI | 4.15 |
| $H_3BO_3$ | 15.5 |
| $MnSo_4 \cdot H_2O$ | 10.5 |
| $ZnSO_4 \cdot 7H_2O$ | 14.4 |
| $Na_2MoO_4 \cdot 2H_2O$ | 0.125 |
| $CuSO_4 \cdot 5H_2O$ | 0.125 |
| $CoCl_2 \cdot 6H_2O$ | 0.125 |
| $FeSO_4 \cdot 7H_2O$ | 27.86 |
| $Na_2EDTA$ | 37.36 |
| Maltose | 25000 |
| Glucose | 10000 |
| myo-Inositol | 100 |
| Casamino acids | 500 |
| L-Glutamine | 1000 |
| L-Arginine | 50 |
| L-Asparagine | 100 |
| L-Alanine | 20 |
| L-Serine | 20 |
| Thiamine-HCl | 1.00 |
| Pyridoxine-HCl | 0.50 |
| Nicotinic acid | 0.50 |
| Glycine | 2.00 |
| Proline | 100 |
| Abscisic Acid | 25 |
| PEG | 100000 |
| Charcoal | 1000 |
| Gelrite[+] | 2500 |
| pH adjusted to 5.7 | |

Mid-Development Assessment and Singulation:

Following seven or eight weeks of development, depending on genotype, the plated embryos were either singulated (individually removed from the ESM mass) to various media modifications of dev B media, or the entire culture square (nylon mesh) was moved en masse to fresh or previously used (cell-contacted) dev B media, or the culture was untouched (control).

Each genotype (A, B, and C) were treated according to the treatment conditions listed below in TABLE 5, with eight replicates per treatment.

TABLE 5

| Mid-development Singulation: Treatment Conditions | | | | |
| --- | --- | --- | --- | --- |
| Treatment # | Treatment of visually mature cotyledonary embryos | post-singulation Media condition | Gelrite concentration (g/L) | % PEG |
| 1 | embryos kept in original cambro box (untouched, unsingulated control) | embryos maintained on original development media (dev B) | 2.5 g/L (dev B) | 10% 10 g/L (dev B) |
| 2 | embryos singulated (picked) and returned to same plate of development media where embryos developed | previously used development media (dev B) (embryos plated onto nylon membrane over media) | 2.5 g/L (dev B) | 10% (dev B) |
| 3 | whole nylon membrane with plated ESM moved to fresh development media (dev B) | fresh development media (dev B) | 0.25 | 10% |
| 4 | singulated embryo (picked) moved to fresh development media | fresh development media (no membrane embryos plated directly onto media) | 0.25 | 10% |

TABLE 5-continued

Mid-development Singulation: Treatment Conditions

| Treatment # | Treatment of visually mature cotyledonary embryos | post-singulation Media condition | Gelrite concentration (g/L) | % PEG |
|---|---|---|---|---|
| 5 | singulated embryos (picked) moved to membrane over fresh development media (dev B) | fresh development media (embryos plated onto nylon membrane over media) | 0.25 | 10% |
| 7 | singulated embryos (picked) moved to fresh development media (dev B) | fresh development media (dev B) (embryos plated onto nylon membrane over media) | 0.30 | 10% |
| 8 | singulated embryo (picked) moved to fresh development media (dev B) | fresh development media (dev B) (embryos plated onto nylon membrane over media) | 0.30 | 5% |
| 9 | singulated embryo (picked) moved to fresh development media (dev B) | fresh development media (dev B) (embryos plated onto nylon membrane over media) | 0.30 | 2.5% |
| 10 | singulated embryo (picked) moved to fresh development media (dev B) | fresh development (dev B) media (embryos plated onto nylon membrane over media) | 0.35 | 10% |
| 11 | singulated embryo (picked) moved to fresh development media (dev B) | fresh development (dev B) media (embryos plated onto nylon membrane over media) | 0.35 | 5% |
| 12 | singulated embryo (picked) moved to fresh development media (dev B) | fresh development (dev B) media (embryos plated onto nylon membrane over media) | 0.35 | 2.5% |

At the time of singulation, all visually mature cotyledonary embryos were hand picked. The criteria for mature embryos to be picked were as follows. All embryos had 4+ cotyledons, no visible greening (this included all shades of green), the presence of distinct cotyledons with hypocotyl and root regions present, no split hypocotyls, and no translucent cotyledons. All embryos, regardless of size, that met the criteria were picked. One technician picked a complete block of plated embryos at a time using a dissecting scope (5-10× magnification).

Post-Singulation Development

Picked embryos were treated under the different treatment conditions shown in TABLE 5 and incubated on the various development media shown in TABLE 5 for an additional four to five weeks, for a total of 12 weeks of total incubation time on development media (including pre-singulation and post-singulation incubation periods).

Post Development Measurements:

Measurements were done at the end of development (week 12) prior to the move to stratification media.

Figure 3:
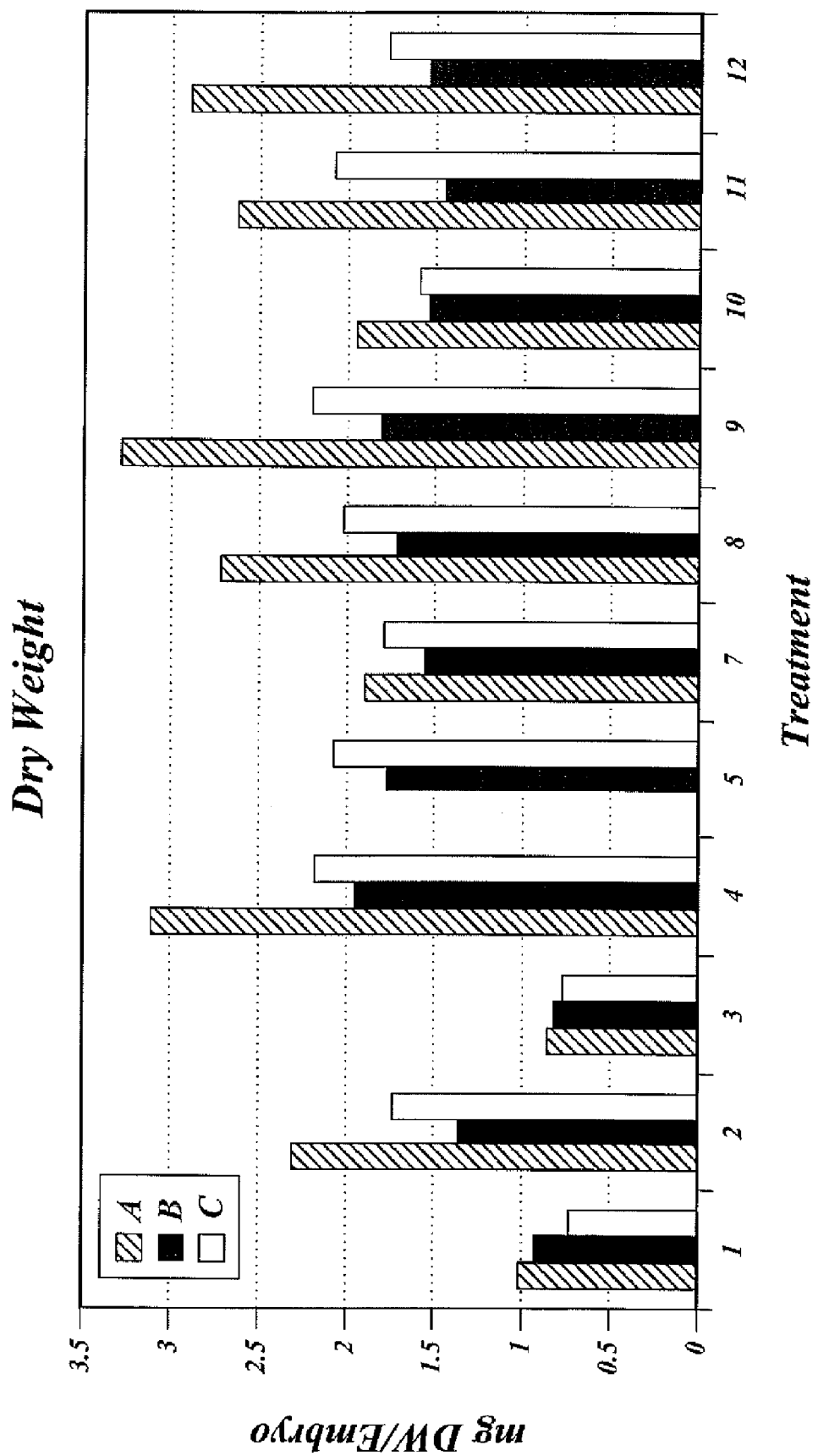
FIG. 3 graphically illustrates the changes in the dry weight per embryo at the end of 12 weeks of development under the treatment conditions described in TABLE 5 for each of the three genotypes A, B, and C, as described in EXAMPLE 3.
Figure 4:
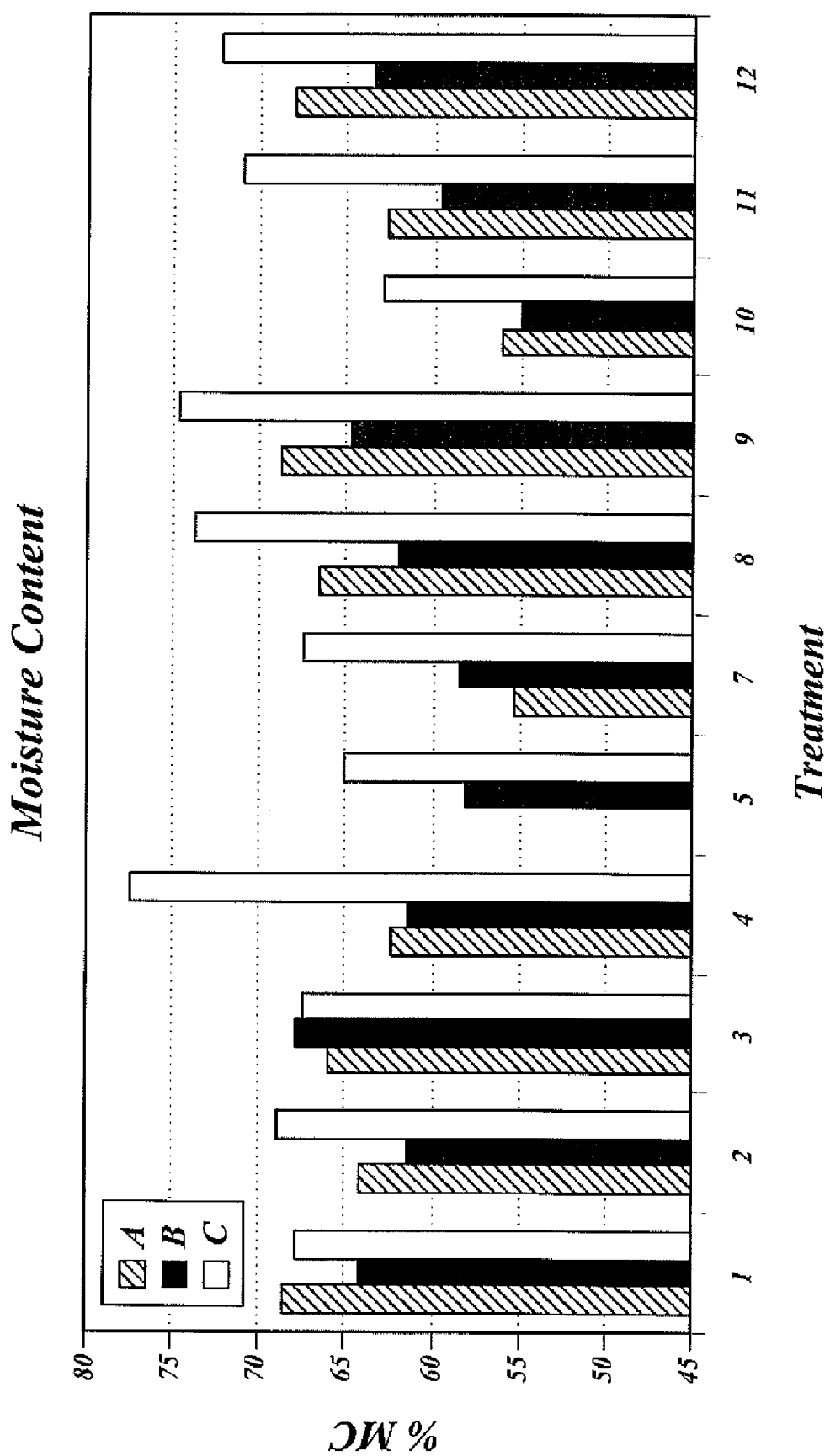
FIG. 4 graphically illustrates the embryo moisture content per embryo at the end of 12 weeks of development under the treatment conditions described in TABLE 5 for each of the three genotypes A, B, and C, as described in EXAMPLE 3.

Dry weight ("DW") and moisture content ("MC") were measured for three replicates per genotype and treatment. The results of dry weight measurements per embryo are shown in FIG. 3. The results of the embryo moisture content per embryo are shown in FIG. 4.

Stratification:

After 12 weeks of development, all embryos or intact cultures were moved to stratification liquid media (20 mls BM5 on a single polyester pad) and placed in the cold at 4° C. on media for four weeks.

Conditioning Over Water:

At the end of stratification, all embryos for germination were moved to dry filter paper placed into small petri plates. The petri dishes were then placed over 500 mls of water for 12-13 days.

Germination:

All embryos were then germinated on 100 mls of germination media BM6 (TABLE 2) in germination boxes for six weeks (1 week in the dark, remainder in light room), then assessed for germination category and organ measurements of Category 1 and 2 germinants.

Assessment of Germination Frequency and Vigor of Germinants:

Germination percentages, dry weight and moisture content were assessed as follows. Each technician working on germination planted an entire block at a time on the same day.

Category 1 germinants ("cat1"): root present and a minimum of 5 epicotyl leaves with a minimum of 5 mm each. Category 1 germinants are transplantable into a greenhouse environment.

Category 2 germinants ("cat2"): root and epicotyl present (bipolar), but epicotyl does not meet the number or length criteria outlined in Category 1.

Bipolar category ("bipolar"): is a combination of Categories 1 and 2.

Category 3 germinants ("cat3"): are embryos with only roots present, and no epicotyl.

Category 1 and Category 2 germinants were evaluated for roots, hypocotyl, cotyledon, epicotyl tuft and epicotyl stem lengths.

Results:

The embryos that were singulated and incubated under the different treatment conditions were examined at the end of development for embryo dry weight and moisture content. FIG. 3 shows the dry weight per embryo at the end of 12 weeks of development under the treatment conditions described in TABLE 4 for each of the three genotypes A, B, and C. Each bar in FIG. 3 represents the mean of three samples. As shown in FIG. 3, singulation of embryos was required for significant increases in embryo dry weight. For example, compare treatment 1 and 3 (not singulated) to treatments 4, 5, and 7-12 (singulated). Singulation of embryos to previously used media (treatment 2) gave intermediate results between treatment 1 (no singulation, same media) and treatment 3 (no singulation, movement to fresh media). The extent of dry weight improvement with singulation varied by genotype, with genotype A the most responsive to singulation.

FIG. 4 graphically illustrates the embryo moisture content by treatment and genotype. Each bar represents the mean of three samples. As shown in FIG. 4, the moisture content measured in embryos from all treatments was above 55%, and most were above 60%.

Germination Data: Results of Pooled Genotype Analysis

Figure 5:
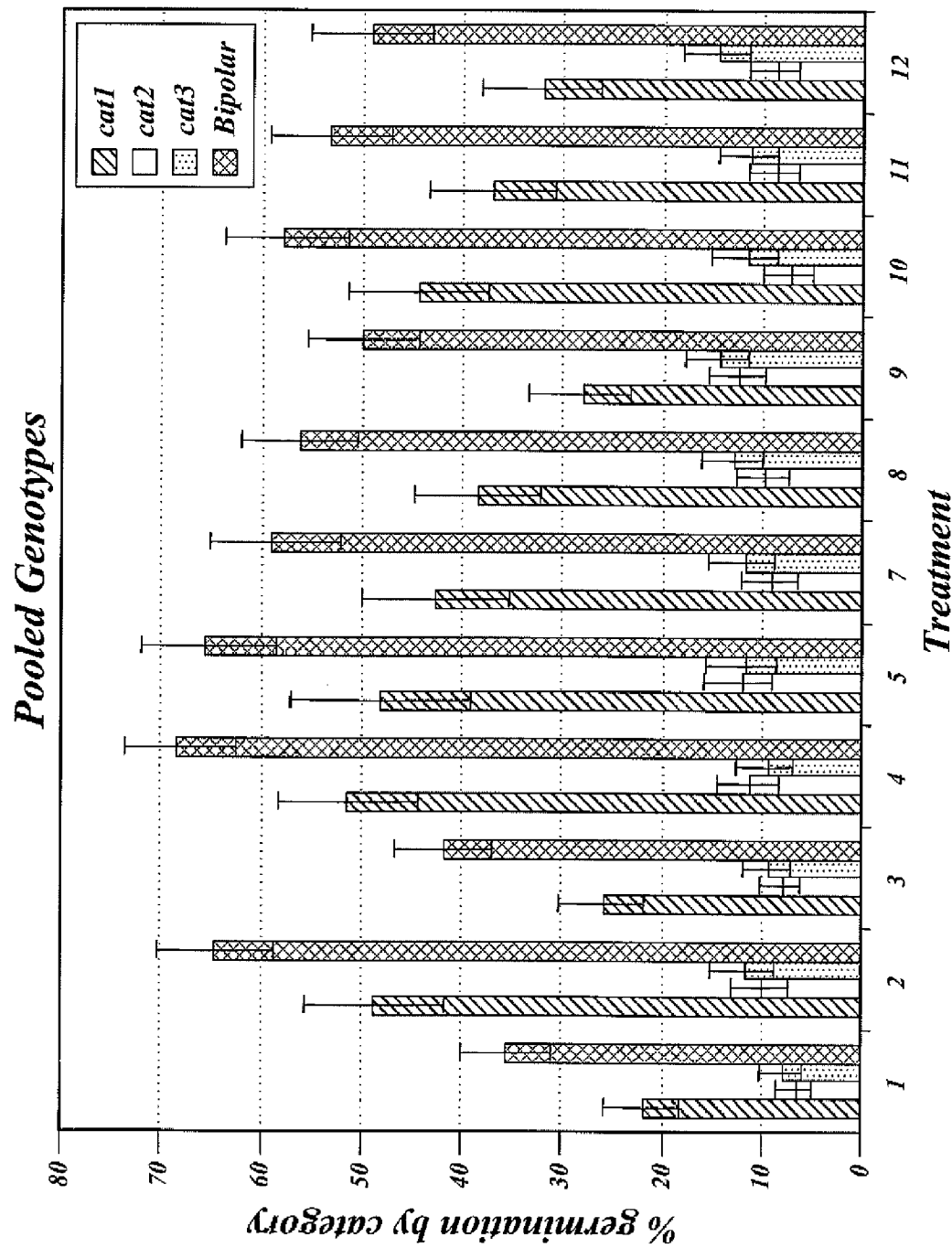
FIG. 5 graphically illustrates the germination percentages of embryos generated using the development treatment conditions described in TABLE 5 based on data pooled across all three genotypes (A, B, and C) for each treatment, as described in EXAMPLE 3.

FIG. 5 graphically illustrates the germination percentages based on data pooled across all three genotypes (A, B, and C) for each treatment with regard to Germination Categories 1, 2, 3 and bipolar germinants. Error bars equal 90% confidence intervals.

As shown in FIG. 5, statistically significant differences ($p<0.001$) in germination percentages were observed between treatment 1 (untouched control) and treatment 2 (singulated to used media), and between treatment 1 and treatment 4 (singulated to fresh media). However, statistically significant differences were not observed ($p=0.22$) between treatment 1 and treatment 3 (whole ESM membrane (unsingulated) moved to fresh media). These results demonstrate that it was the singulation step and not the differences in media that was the most critical parameter for increased germination frequency within the parameters tested in this experiment.

TABLE 6 shows the pooled genotype data for root length, hypocotyl length, cotyledon length, epicotyl length and epicotyl stem length for Category 1 germinants.

TABLE 6

| Category 1 germinant organ lengths, pooled genotypes | | | | | |
| --- | --- | --- | --- | --- | --- |
| Treatment | Root length (mm) | Hypocotyl length (mm) | Cotyledon length (mm) | Epicotyl length (mm) | Epicotyl stem (mm) |
| 1 | 17.6 | 7.6 | 4.3 | 9.9 | 0.9 |
| 2 | 28.2* | 9.5* | 5.5* | 12.8* | 1.1 |
| 3 | 17.7 | 8.6 | 4.8 | 10.8 | 1.0 |
| 4 | 29.1* | 10.0* | 6.6* | 14.0* | 1.2 |
| 5 | 27.4 | 10.4* | 6.4* | 13.5* | 1.0 |
| 7 | 26.9 | 10.1* | 6.2* | 12.7* | 1.3 |
| 8 | 28.4* | 10.1* | 6.5* | 12.6* | 1.1 |
| 9 | 27.4 | 10.3* | 6.5* | 12.3* | 0.9 |
| 10 | 28.8* | 10.1* | 5.8* | 13.4* | 1.5 |
| 11 | 28.7* | 10.7* | 6.5* | 12.7* | 1.3 |
| 12 | 26.3 | 9.9* | 6.2* | 12.2* | 1.0 |

*Indicates a value statistically different from Treatment 1 ($p = 0.05$ or less)

The data in TABLE 6 demonstrates statistically significant differences in organ length between treatment 1 (control) and treatment 2 (singulated to used media), and between treatment 1 and treatment 4 (singulated to fresh media). However, a significant difference was not observed between treatment 1 and treatment 3 (whole ESM membrane (unsingulated) moved to fresh media). These results are consistent with those observed in FIG. 5, as described above. Of particular note is the statistically significant ($p=0.05$) increase in root length which is 1.6× greater in either treatment 2 or 4 (as well as other singulated treatments) as compared to treatment 1 or treatment 3 (unsingulated controls), where the differences observed were not statistically significant ($p=1.0$).

Germination Data: Results of Individual Genotype Analysis

Figure 6:
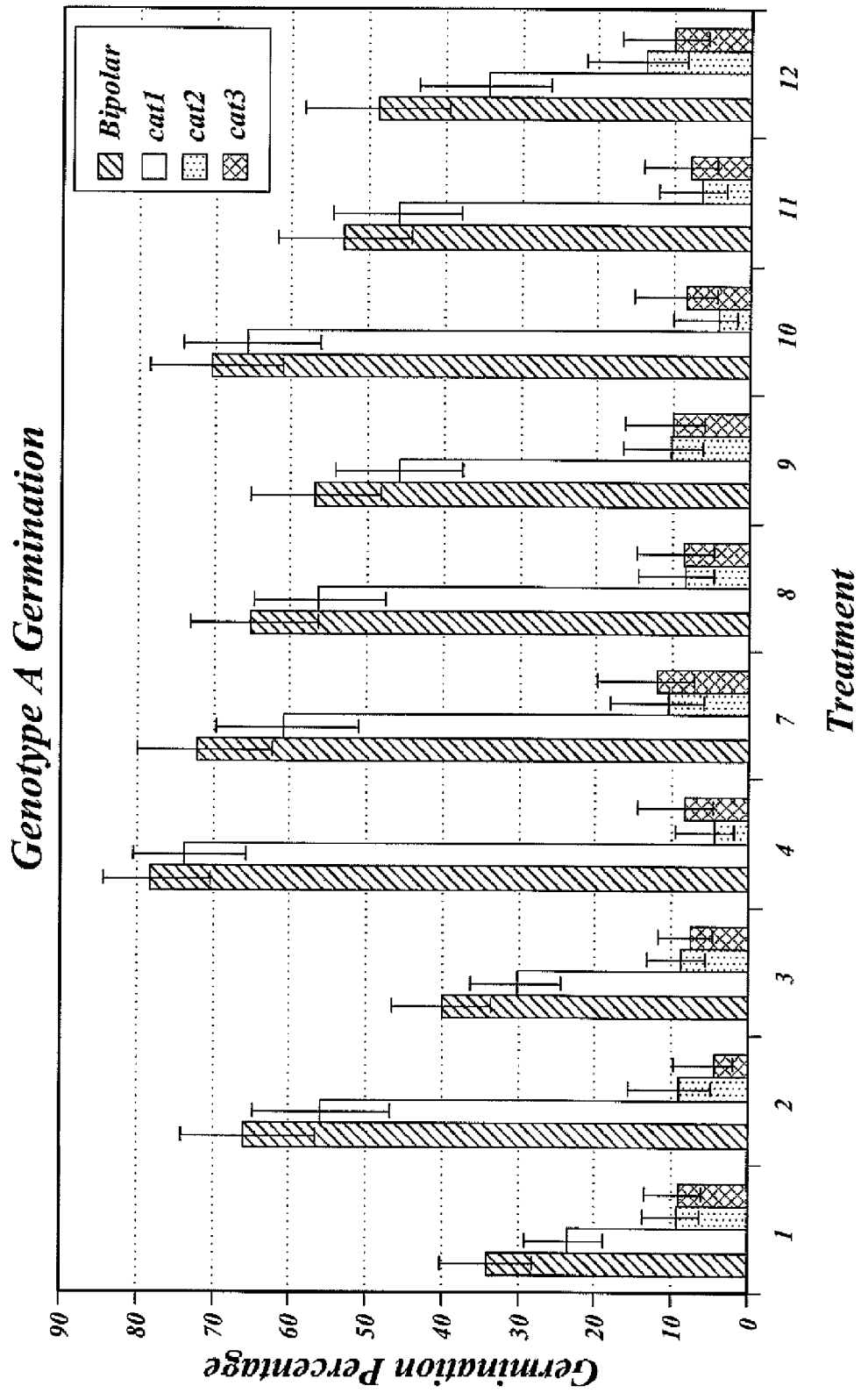
FIG. 6 graphically illustrates the germination percentages for genotype A by treatment described in TABLE 5, with regard to Category 1, 2, and 3 germinants and bipolar germinants, as described EXAMPLE 3.
Figure 7:
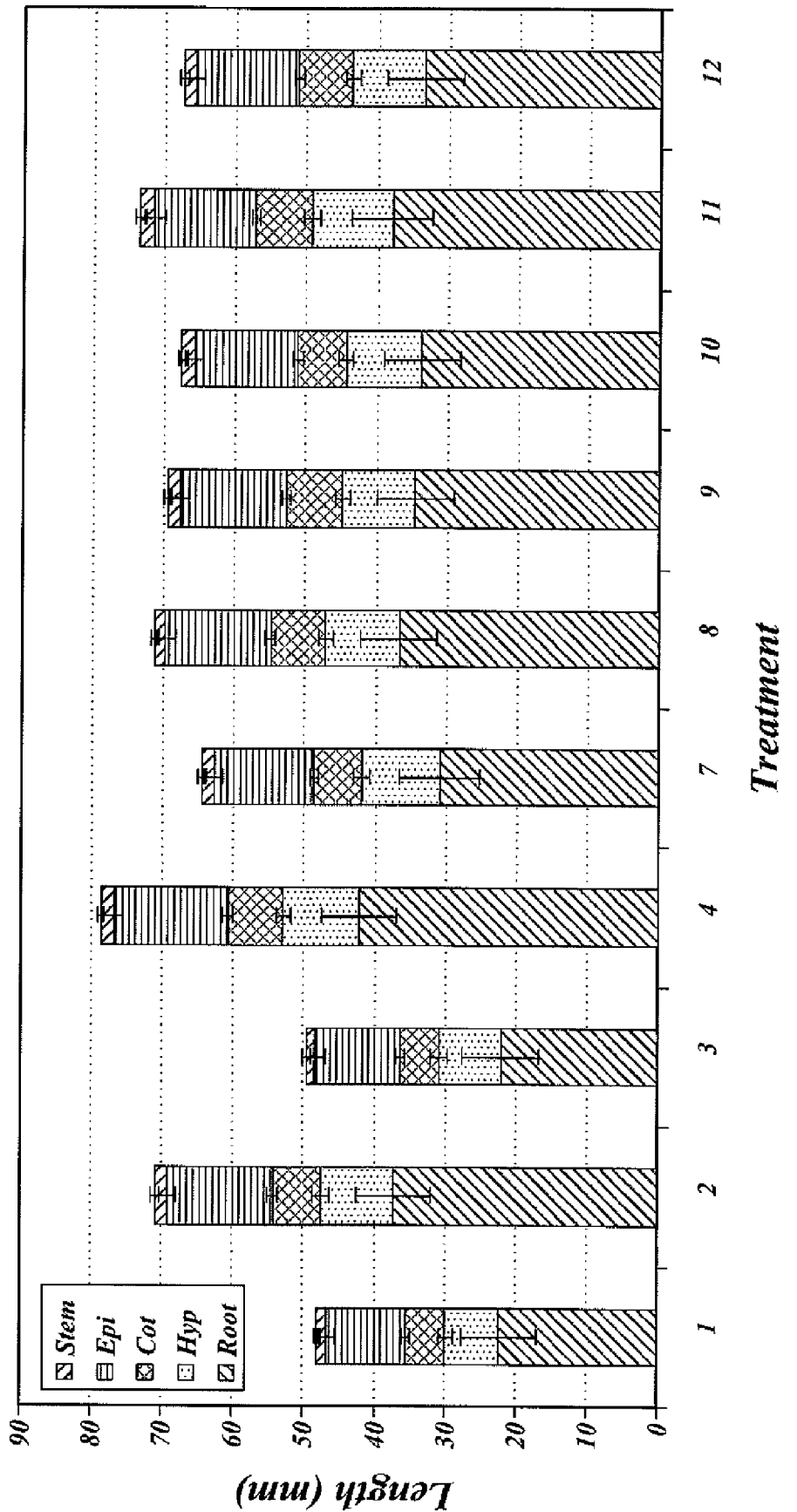
FIG. 7 graphically illustrates the data for genotype A for Category 1 germinants by treatment described in TABLE 5, with regard to germinant root length, hypocotyl length, cotyledon length, epicotyl length and epicotyl stem length, as described in EXAMPLE 3.

FIG. 6 graphically illustrates the germination percentages for genotype A by treatment with regard to Categories 1, 2, and 3 germinants and bipolar germinants. Bars equal 90% confidence intervals. FIG. 7 graphically illustrates the data for genotype A for Category 1 germinants by treatment with regard to germinant root length ("root"), hypocotyl length ("hyp"), cotyledon length ("cot"), epicotyl length ("epi") and epicotyl stem length ("stem").

Figure 8:
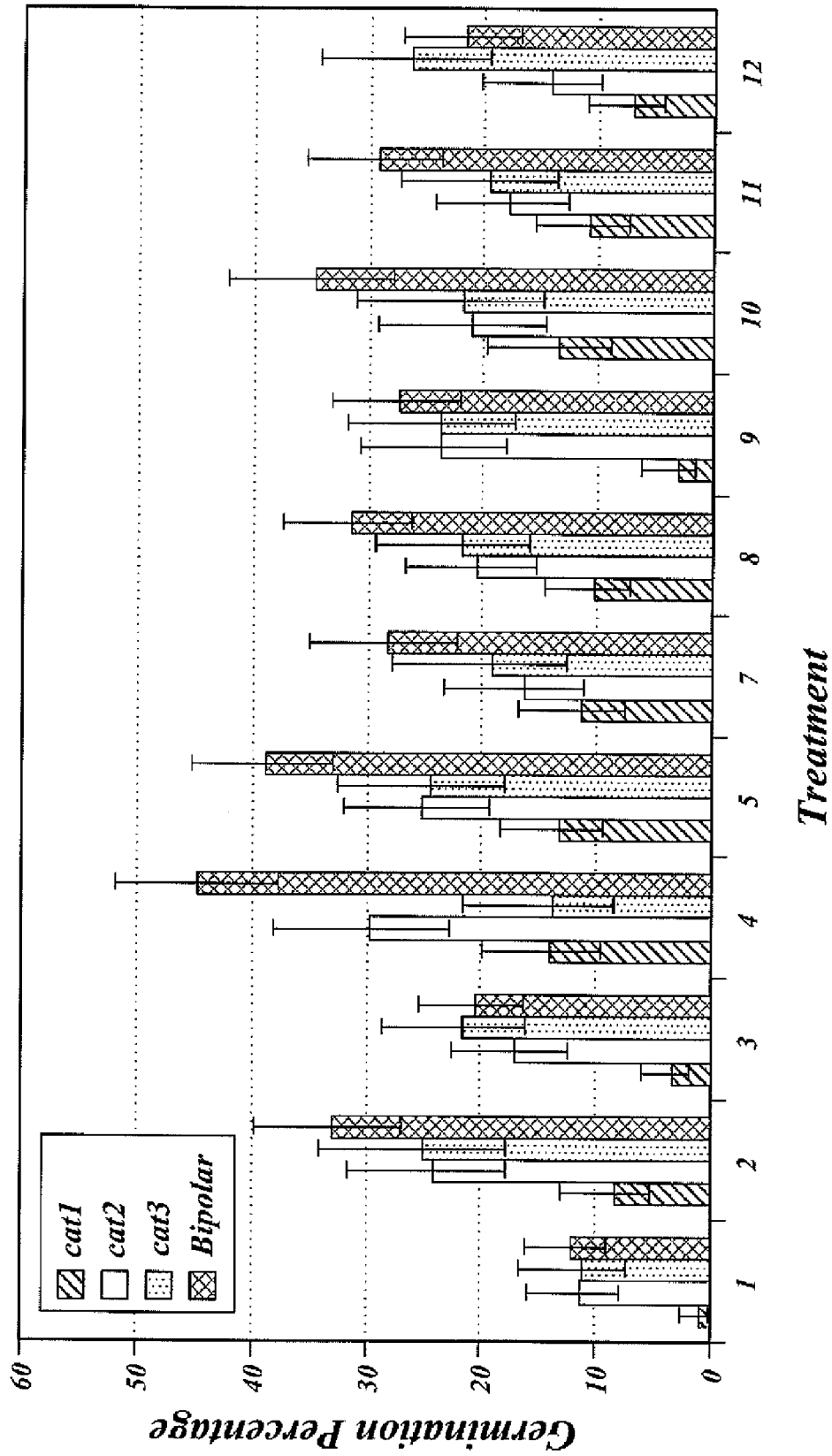
FIG. 8 graphically illustrates the germination percentages for genotype B by treatment described in TABLE 5 with regard to Category 1, 2, and 3 germinants and bipolar germinants, as described in EXAMPLE 3.
Figure 9:
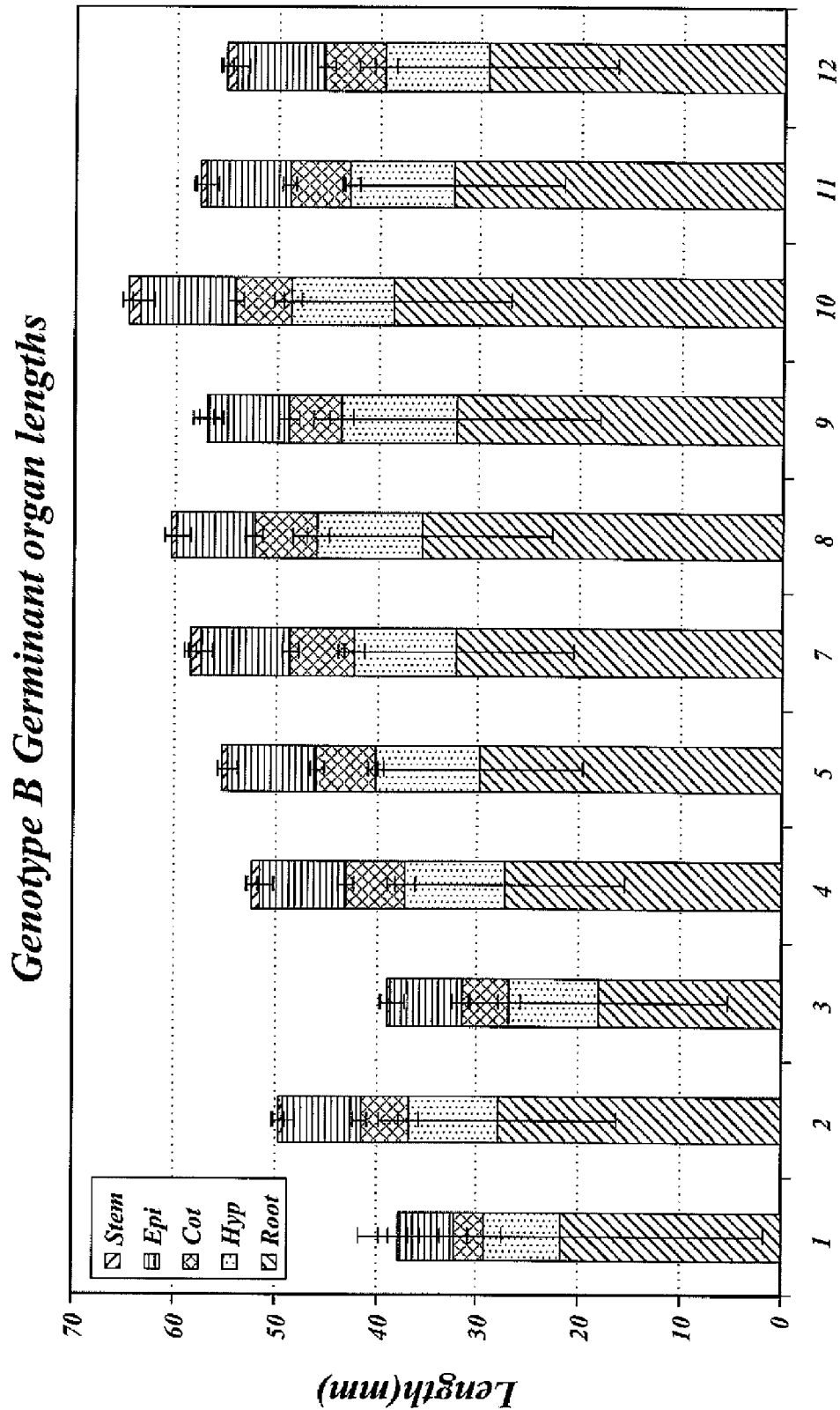
FIG. 9 graphically illustrates the data for genotype B for Category 1 germinants by treatment described in TABLE 5 with regard to germinant root length, hypocotyl length, cotyledon length, epicotyl length and epicotyl stem length, as described in EXAMPLE 3.

FIG. 8 graphically illustrates the germination percentages for genotype B by treatment with regard to Category 1, 2, and 3 germinants and bipolar germinants. Bars equal 90% confidence intervals. FIG. 9 graphically illustrates the data for genotype B for Category 1 germinants by treatment with regard to germinant root length, hypocotyl length, cotyledon length, epicotyl length and epicotyl stem length.

FIG. 10 graphically illustrates the germination percentages for genotype C by treatment with regard to Category 1, 2, and 3 germinants and bipolar germinants. Bars equal 90% confidence intervals. FIG. 11 graphically illustrates the data for genotype C for Category 1 germinants by treatment with regard to germinant root length, hypocotyl length, cotyledon length, epicotyl length and epicotyl stem length.

Summary of Results:

The pooled data across the three genotypes (A, B, and C) tested showed the same trends as the results from the individual genotypes. Statistically significant differences ($p=<0.001$) between treatment 1 and both treatment 2 and treatment 4 were observed, but significant differences were not observed between treatment 1 and treatment 3 ($p=0.22$). These results demonstrate that early singulation during development, and not differences in media, is the most critical variable for improving germination percentage and germinant vigor, within the context of the parameters tested in this experiment.

With regard to vigor of germinants, the genotype pooled data shows significant differences between organ length after treatment with treatments 1 and 2 or 4, but not treatment 3. Of particular note is the significant difference ($p=0.05$) increase in root length, which is 1.6× greater in either treatment 2 or 4 (as well as other treatments) as compared to treatments 1 and 3, which did not differ ($p=1.0$).

With regard to germinant vigor measurements, the most pertinent category for looking for quality improvement is Category 1 germination, which is equivalent to a transplantable embryo into a greenhouse environment. The pattern for dry weight differences in treatments 1-4, shown in FIG. 3, is closely manifested in germination percentage for Category 1 germination, shown in FIG. 6. For example, as shown in FIG. 6, germination percentage for Genotype A was improved by over 40 basis points by singulating embryos during development and moving the singulated embryos to fresh media as compared to the unsingulated, untouched control.

The data from the individual genotypes follows the same trends as the pooled data described above. The germination percentage results demonstrates that all three genotypes (A, B, and C), shown in FIG. 6, FIG. 8 and FIG. 10, respectively, responded similarly to the treatment conditions shown in TABLE 5, despite the different basal levels of germination in the untouched controls (treatment 1, TABLE 5).

Germination percentage for genotype B was the lowest of the three genotypes tested, but the relative pattern was similar to genotypes A and C for treatments 1-4 (see FIGS. 8 and 9). A 34 basis point improvement in the best early singulation treatment 4 was observed as compared to the untouched, unsingulated control (see FIG. 8).

Germination percentage for Genotype C of control embryos (60+%), as shown in FIG. 10, was higher than for Genotype A (shown in FIG. 6), with an improvement of 20 basis points after singulating and moving embryos to either original or fresh media as compared to the untouched (unsingulated) control. For genotype C, Category 1 germinant organ lengths were also improved by early singulation to either old or fresh media, as shown in FIG. 11.

Similarly, germinant morphology of Category 1 germinants (FIG. 7) for treatments 1-4 also matched dry weight and germination data (and less so for the remaining treatments).

TABLE 7

Germination Percentage (Category 1) of unsingulated (treatment 1)
versus singulated (treatment 4) embryos for each genotype tested.

| Genotype | Control (treatment 1) | Early Singulated (Treatment 4) | Change in % |
| --- | --- | --- | --- |
| A | 22% | 72% | 50 |
| B | 12% | 45% | 32 |
| C | 62% | 78% | 16 |

CONCLUSIONS

These results demonstrate the surprising observation that early singulation from the embryonal suspensor mass (ESM) improves germination success in the three genotypes tested, and also increases the vigor of the germinants.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of increasing germination vigor of pine somatic embryos produced in vitro, the method comprising:
    (a) singulating a plurality of individual immature pine somatic embryos from a first culture of embryos after a first incubation period in a first development media; and
    (b) contacting the plurality of singulated immature pine somatic embryos with a second development media for a second incubation period.

2. The method of claim 1, wherein the first culture of embryos is an embryonal suspensor mass.

3. The method of claim 1, wherein the first incubation period is a time period sufficient in length for the formation of one or more cotyledonary primordia on a portion of the plurality of immature pine somatic embryos in the first culture of embryos.

4. The method of claim 1, wherein the first incubation period is at least six weeks.

5. The method of claim 1, wherein the first incubation period is from seven weeks to eight weeks.

6. The method of claim 1, wherein the second incubation period is sufficient in length for at least a portion of the plurality of the singulated immature pine somatic embryos to reach anatomical maturity.

7. The method of claim 1, wherein the second incubation period is from three weeks to five weeks.

8. The method of claim 1, wherein the combination of the first incubation period and the second incubation period totals a time period of at least 12 weeks.

9. The method of claim 1, wherein the singulating step comprises picking the plurality of individual immature pine somatic embryos from the first culture of embryos.

10. The method of claim 9, wherein the plurality of embryos are picked based on a criterion selected from the group consisting of embryo size, embryo shape, embryo surface texture and embryo color.

11. The method of claim 2, wherein the singulating step comprises removing the embryonal suspensor mass from the plurality of individual immature pine somatic embryos.

12. The method of claim 11, wherein the singulating step comprises washing away at least a portion of the embryonal suspensor mass from the plurality of individual embryos.

13. The method of claim 1, wherein the singulated immature pine somatic embryos contacted with the second development medium are not in physical contact with one another.

14. The method of claim 1, further comprising transferring the singulated immature pine somatic embryos to a porous substrate prior to step (b).

15. The method of claim 1, wherein the osmolality of the first development medium is in the range of from 300 mM/Kg to 400 mM/Kg.

16. The method of claim 1, wherein the first development media comprises PEG at a concentration of from about 1% to about 10%.

17. The method of claim 1, wherein the osmolality of the second development media is in the range of from 350 mM/Kg to 450 mM/Kg.

18. The method of claim 1, wherein the second development media comprises PEG at a concentration range of about 7% to about 15%.

19. The method of claim 1, wherein the somatic embryos are Loblolly pine.

* * * * *